US012624005B2

(12) United States Patent
Canturk et al.

(10) Patent No.: US 12,624,005 B2
(45) Date of Patent: May 12, 2026

(54) SYNTHESIS OF 4-AMINO-6-(HETEROCYCLIC)PICOLINATES

(71) Applicant: CORTEVA AGRISCIENCE LLC, Indianapolis, IN (US)

(72) Inventors: Belgin Canturk, Carmel, IN (US); Jayachandran Devaraj, Zionsville, IN (US); Amaruka Hazari, Carmel, IN (US); Christopher Kassl, Hoffman Estates, IL (US); Melissa Lee, Indianapolis, IN (US); Fangzheng Li, Carmel, IN (US); Christian T. Lowe, Westfield, IN (US); Thomas L. Siddall, Zionsville, IN (US); Gregory T. Whiteker, Carmel, IN (US); Chunming Zhang, Zionsville, IN (US)

(73) Assignee: CORTEVA AGRISCIENCE LLC, IN (US)

( * ) Notice: Subject to any disclaimer, the term of this patent is extended or adjusted under 35 U.S.C. 154(b) by 768 days.

(21) Appl. No.: 17/932,334

(22) PCT Filed: Mar. 17, 2021

(86) PCT No.: PCT/US2021/022716

§ 371 (c)(1),
(2) Date: Sep. 15, 2022

(87) PCT Pub. No.: WO2021/188639

PCT Pub. Date: Sep. 23, 2021

(65) Prior Publication Data

US 2023/0357155 A1 Nov. 9, 2023

Related U.S. Application Data

(60) Provisional application No. 62/991,291, filed on Mar. 18, 2020.

(51) Int. Cl.

| | |
|---|---|
| ***C07D 213/803*** | (2006.01) |
| ***C07D 209/04*** | (2006.01) |
| ***C07D 401/04*** | (2006.01) |
| ***C07F 5/02*** | (2006.01) |
| ***C07F 7/10*** | (2006.01) |

(52) U.S. Cl.

CPC ....... *C07D 213/803* (2013.01); *C07D 209/04* (2013.01); *C07D 401/04* (2013.01); *C07F 5/02* (2013.01); *C07F 7/10* (2013.01)

(58) Field of Classification Search

CPC .................................................. C07D 213/803

See application file for complete search history.

(56) References Cited

U.S. PATENT DOCUMENTS

| | | | | |
|---|---|---|---|---|
| 8,871,943 | B2 * | 10/2014 | Renga ................ | C07D 213/803 546/310 |
| 9,067,890 | B2 * | 6/2015 | Arndt ................... | C07D 213/81 |
| 9,452,984 | B2 * | 9/2016 | Arndt ................... | C07D 213/84 |
| 10,087,164 | B2 * | 10/2018 | Fisk ..................... | C07D 213/79 |
| 2012/0190857 | A1 | 7/2012 | Arndt et al. | |
| 2014/0274695 | A1 | 9/2014 | Eckelbarger et al. | |

FOREIGN PATENT DOCUMENTS

WO 2018/208582 A1 11/2018

OTHER PUBLICATIONS

International Preliminary Report on Patentability for International Application No. PCT/US2021/022716, mailed Sep. 29, 2022, 7 pages.

International Search Report and Written Opinion for International Application No. PCT/US21/22716, mailed May 11, 2021.

* cited by examiner

*Primary Examiner* — Golam M Shameem

(57) ABSTRACT

The present disclosure relates to improved processes for preparing 4-amino-6-(heterocyclic)picolinates.

18 Claims, No Drawings

SYNTHESIS OF 4-AMINO-6-(HETEROCYCLIC)PICOLINATES

CROSS-REFERENCE TO RELATED APPLICATIONS

This application claims priority to International (PCT) Patent Application Serial No. PCT/US21/22716, filed Mar. 17, 2021, and entitled "IMPROVED SYNTHESIS OF 4-AMINO-6-(HETEROCYCLIC) PICOLINATES," which claims priority to U.S. Provisional Application Ser. No. 62/991,291, filed on Mar. 18, 2020, the entire disclosure of which is hereby expressly incorporated by reference.

FIELD

The present disclosure concerns improved processes for the preparation of 4-amino-6-(heterocyclic)picolinates. More particularly, the present disclosure concerns an improved process for the preparation of 4-amino-6-(heterocyclic)picolinates from 6-bromo-4-aminopicolinates.

BACKGROUND 4-amino-6-(heterocyclic)picolinates, such as arylalkyl and alkyl 4-amino-3-chloro-5-fluoro-6-(4-chloro-2-fluoro-3-methoxyphenyl)picolinates, are high value herbicides recently developed and marketed by Dow AgroSciences LLC. PCT Patent Application Publication WO 2018208582 A1, U.S. Patent Application Publication 20120190857 A1, and U.S. Pat. Nos. 7,314,849 B2, 8,609,853 B2, 8,609,855

B2, 8,754,231 B2, 8,836,688 B2, 9,637,505 B2, 10,087,164 B2, 10,544,121 B2, and 10,570,114 B2 (the disclosure of each is explicitly incorporated by reference herein) describe inter alia certain 4-amino-6-aryl- and -6-heteroarylpicolinates and syntheses thereof. The syntheses of these molecules involve reacting a 6-chloropicolinic acid or 6-chloropicolinate head with an aryl or a heteroaryl boronic acid or boronate tail. The reaction scheme for 4-amino-6-arylpicolinates is shown in Scheme 1.

Scheme 1

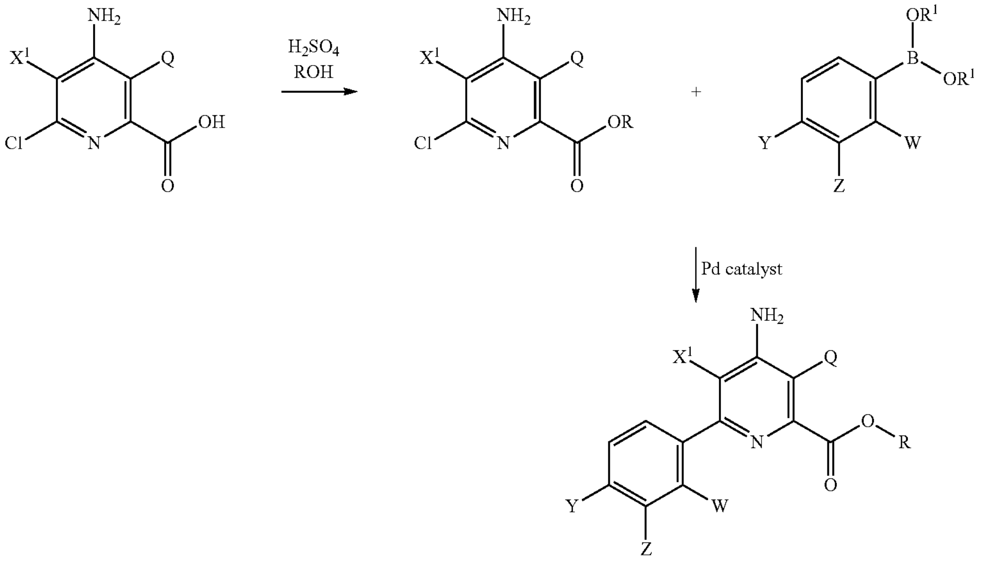

Q = H or Cl;
R = alkyl or arylalkyl;
$R^1$ = H, alkyl, or branched alkyl;
W = H, F, alkyl, or alkoxy;
$X^1$ = H, F, or Cl;
Y = Cl; and
Z = alkoxy It would be useful to have a higher yielding process route to these 6-aryl- and 6-heteroaryl-4-aminopicolinate compounds.

SUMMARY

The present disclosure concerns an improved process for the preparation of 4-amino-6-(heterocyclic)picolinates and picolinonitriles of Formula I.

In some embodiments, the disclosure concerns a process for the preparation of 4-amino-6-(heterocyclic)picolinates of Formula I Formula I

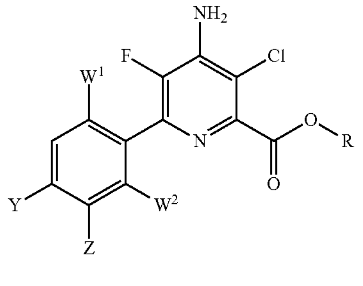

wherein

R represents H, $C_1$-$C_{12}$ alkyl, $C_3$-$C_{12}$ alkynyl, $C_1$-$C_3$ alkyl substituted with CN, or $C_6$-$C_{12}$ arylalkyl;

$W^1$ represents H or F;

$W^2$ represents H, F, Cl, $C_1$-$C_3$ alkyl, or $C_1$-$C_3$ alkoxy;

Y represents H, halogen, $C_1$-$C_4$ alkyl, $C_1$-$C_4$ haloalkyl, $C_1$-$C_3$alkoxy, $C_1$-$C_3$ haloalkoxy, —CN, or —$NO_2$; and Z represents H, F, Cl, $C_1$-$C_4$ alkyl, $C_1$-$C_3$alkoxy, $C_1$-$C_4$ haloalkyl, $C_1$-$C_3$ haloalkoxy, $C_1$-$C_3$ alkoxy-substituted $C_1$-$C_3$ alkyl, or —$NR^1R^2$, wherein $R^1$ and $R^2$ are independently hydrogen, $C_1$-$C_3$ alkyl, or $C_1$-$C_3$ haloalkyl; or Y and Z or Z and $W^2$ taken together are a 5-membered aromatic or non-aromatic, heterocyclic ring;

the process comprising the following steps:

a) creating a first mixture containing a compound of Formula A,

Formula A

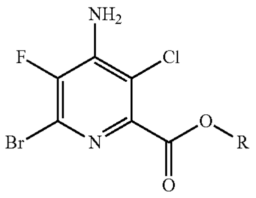

wherein

R represents H, $C_1$-$C_{12}$ alkyl, $C_3$-$C_{12}$ alkynyl, $C_1$-$C_3$ alkyl substituted with CN, or $C_6$-$C_{12}$ arylalkyl;

a compound of Formula B1 or Formula B2, or mixtures thereof,

Formula B1

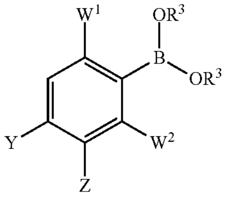

Formula B2

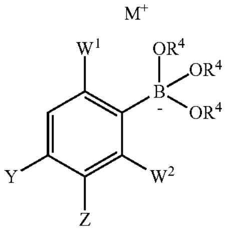

wherein $M^+$ represents an alkali metal cation;

$R^3$ represents H or $C_1$-$C_6$ alkyl, or alternatively two $R^3$ may form a $C_2$-$C_6$ alkyl linkage, which together with B and two O form a 5- to 9-atom cyclic structure;

$R^4$ represents $C_1$-$C_6$ alkyl;

$W^1$ represents H or F;

$W^2$ represents H, F, Cl, $C_1$-$C_3$ alkyl, or $C_1$-$C_3$ alkoxy;

Y represents H, halogen, $C_1$-$C_4$ alkyl, $C_1$-$C_4$ haloalkyl, $C_1$-$C_3$alkoxy, $C_1$-$C_3$ haloalkoxy, —CN, or —$NO_2$; and Z represents H, F, Cl, $C_1$-$C_4$ alkyl, $C_1$-$C_3$alkoxy, $C_1$-$C_4$ haloalkyl, $C_1$-$C_3$ haloalkoxy, $C_1$-$C_3$ alkoxy-substituted $C_1$-$C_3$ alkyl, or —$NR^1R^2$, wherein $R^1$ and $R^2$ are independently hydrogen, $C_1$-$C_3$ alkyl, or $C_1$-$C_3$ haloalkyl; or Y and Z or Z and $W^2$ taken together are a 5-membered aromatic or non-aromatic, heterocyclic ring;

one or more bases; and one or more solvents;

b) adding a palladium catalyst, and optionally a ligand to the first mixture to form a second mixture; and c) heating the second mixture to a temperature of between about 25° C. and about 100° C.

Specific examples of the heterocyclic group in Formula I can be found in PCT International Application Publication Nos. WO 2014151005 and WO 2014151009, the disclosures of which are explicitly incorporated herein by reference and include, but are not limited to, the following examples T1 to T36:

T1

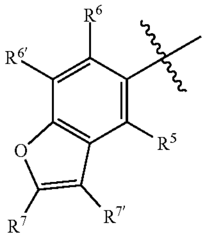

T2

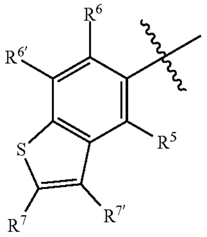

T3

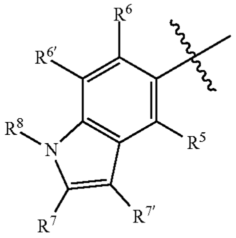

T4

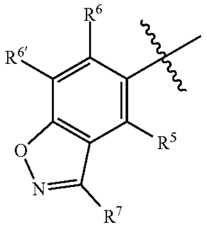

T5

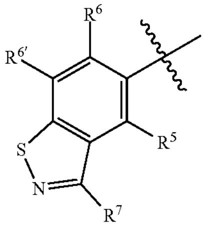

-continued
T6
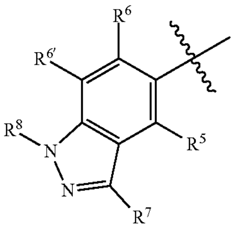
T7
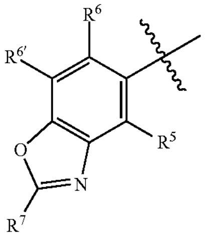
T8
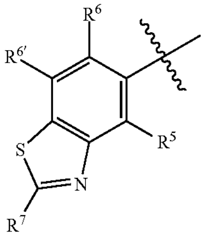
T9
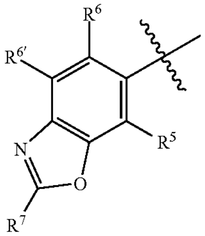
T10
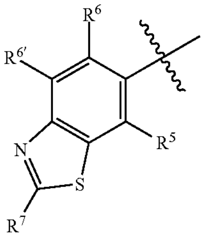
T11
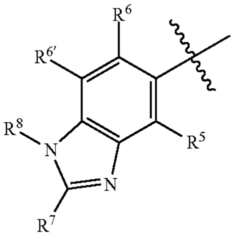
-continued
T12
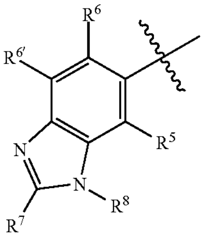
T13
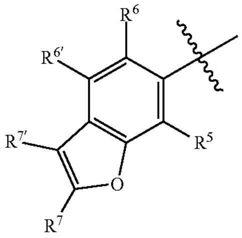
T14
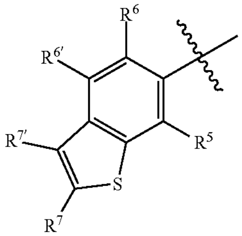
T15
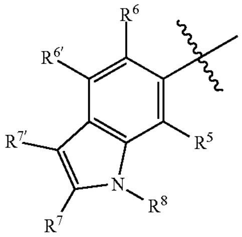
T16
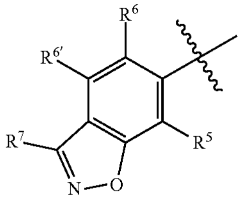
T17
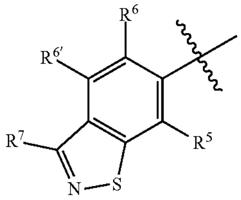
T18
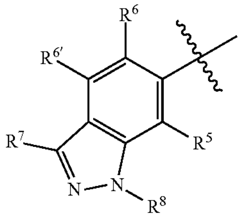

-continued
T19
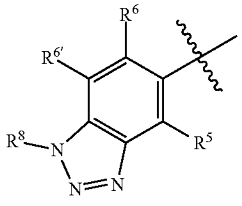
T20
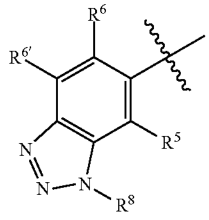
T21
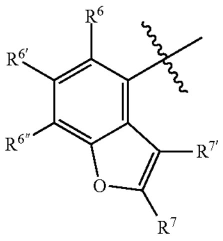
T22
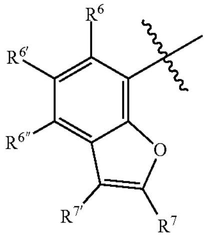
T23
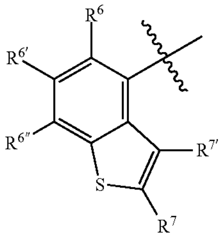
T24
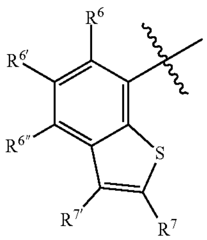
-continued
T25
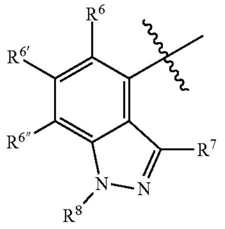
T26
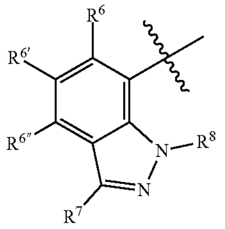
T27
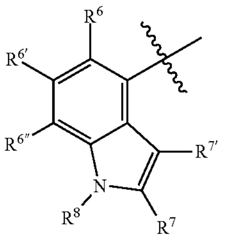
T28
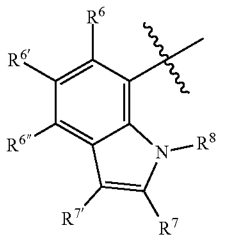
T29
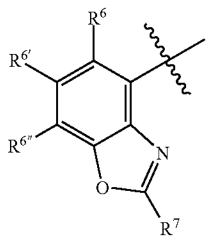
T30
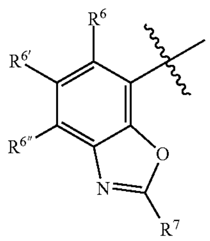

-continued

T31

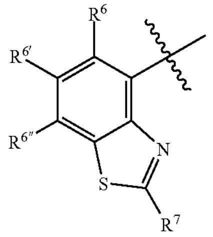

T32

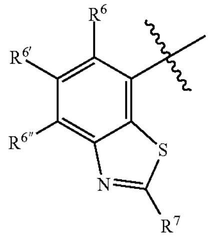

T33

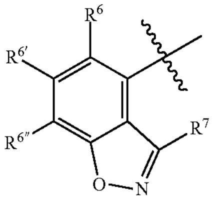

T34

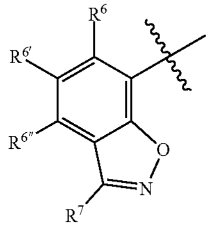

T35

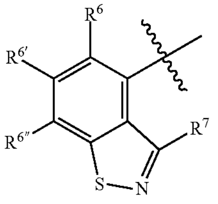

T36

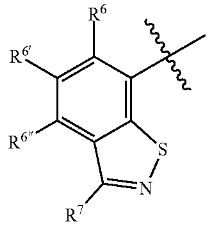

$R^5$, if applicable to the A group, is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$, if applicable to the A group, are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_1$-$C_4$ haloalkylamino, or phenyl;

$R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alknyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl.

The components of each mixture listed in the steps above such as Formula A, Formula B, the one or more bases, and the one or more solvents used to form the first mixture may be combined in a different order than specified. The order in which the components are added to form the mixtures in the present disclosure is not limited to the order illustrated.

DETAILED DESCRIPTION

As used herein, the term "alkyl" refers to saturated hydrocarbon moieties that are straight-chained or branched. Unless otherwise specified, $C_1$-$C_{20}$ (e.g., $C_1$-$C_{12}$, $C_1$-$C_8$, $C_1$-$C_6$, $C_1$-$C_4$) alkyl groups are intended. Examples of alkyl groups include, but are not limited to, methyl, ethyl, propyl, butyl, isopropyl, isobutyl, tertiary butyl, pentyl, and hexyl.

As used herein, the term "cycloalkyl" refers to saturated hydrocarbon moieties that are cyclic. Examples of cycloalkyl groups include, but are not limited to, cyclopropyl, cyclobutyl, cyclopentyl, cyclohexyl, and the like. Alkyl and cycloalkyl substituents may be unsubstituted or substituted with one or more chemical moieties. Examples of suitable substituents include, for example, hydroxy, nitro, cyano, formyl, $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$alkoxycarbonyl, $C_1$-$C_6$ haloalkoxycarbonyl, $C_1$-$C_6$ carbamoyl, $C_1$-$C_6$ halocarbamoyl, hydroxycarbonyl, $C_1$-$C_6$ alkylcarbonyl, $C_1$-$C_6$haloalkylcarbonyl, aminocarbonyl, $C_1$-$C_6$alkylaminocarbonyl, haloalkylaminocarbonyl, $C_1$-$C_6$ dialkylaminocarbonyl, and $C_1$-$C_6$ dihaloalkylaminocarbonyl, provided that the substituents are sterically compatible and the rules of chemical bonding and strain energy are satisfied. Preferred substituents include cyano and $C_1$-$C_6$ alkoxy.

As used herein, the terms "haloalkyl" and "halocycloalkyl" refer to alkyl and cycloalkyl groups, respectively, as defined above, wherein these groups the hydrogen atoms may be partially or entirely substituted with halogen atoms. Unless otherwise specified, $C_1$-$C_{20}$ (e.g., $C_1$-$C_{12}$, $C_1$-$C_{10}$, $C_1$-$C_4$) alkyl groups are intended. Examples include, but are not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, and 1,1,1-trifluoroprop-2-yl. Haloalkyl substituents may be unsubstituted or substituted with one or more chemical moieties. Examples of suitable substituents include, for example, hydroxy, nitro, cyano, formyl, $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$alkoxycarbonyl, $C_1$-$C_6$ haloalkoxycarbonyl, $C_1$-$C_6$ carbamoyl, $C_1$-$C_6$ halocarbamoyl, hydroxycarbonyl, $C_1$-$C_6$ alkylcarbonyl, $C_1$-$C_6$haloalkylcarbonyl, aminocarbonyl, $C_1$-$C_6$alkylaminocarbonyl, haloalkylaminocarbonyl, $C_1$-$C_6$ dialkylaminocarbonyl, and $C_1$-$C_6$ dihaloalkylaminocarbonyl, provided that the substituents are sterically compatible and the rules of chemical bonding and strain energy are satisfied. Preferred substituents include cyano and $C_1$-$C_6$ alkoxy.

As used herein, the term "alkenyl" refers to unsaturated, straight-chained, or branched hydrocarbon moieties containing a double bond. Unless otherwise specified, $C_2$-$C_{20}$ (e.g., $C_2$-$C_{12}$, $C_2$-$C_{10}$, $C_2$-$C_8$, $C_2$-$C_6$, $C_2$-$C_4$) alkenyl groups are intended. Alkenyl groups may contain more than one unsaturated bond. Examples include, but are not limited to, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, and the like. The term "vinyl" refers to a group having the structure $-CH=CH_2$; 1-propenyl refers to a group with the structure-$CH=CH-CH_3$; and 2-propenyl refers to a group with the structure $-CH_2-CH=CH_2$. Alkenyl substituents may be unsubstituted or substituted with one or more chemical moieties. Examples of suitable substituents include, but are not limited to, hydroxy, nitro, cyano, formyl, $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkoxycarbonyl, $C_1$-$C_6$haloalkoxycarbonyl, $C_1$-$C_6$ carbamoyl, $C_1$-$C_6$halocarbamoyl, hydroxycarbonyl, $C_1$-$C_6$alkylcarbonyl, $C_1$-$C_6$haloalkylcarbonyl, aminocarbonyl, $C_1$-$C_6$ alkylaminocarbonyl, haloalkylaminocarbonyl, $C_1$-$C_6$ dialkylaminocarbonyl, and $C_1$-$C_6$ dihaloalkylaminocarbonyl, provided that the substituents are sterically compatible and the rules of chemical bonding and strain energy are satisfied. In some embodiments, the substituents include cyano and $C_1$-$C_6$ alkoxy.

The term "haloalkenyl," as used herein, refers to an alkenyl group, as defined above, which is substituted by one or more halogen atoms.

As used herein, the term "alkynyl" represents straight-chained or branched hydrocarbon moieties containing a triple bond. Unless otherwise specified, $C_2$-$C_{20}$ (e.g., $C_2$-$C_{12}$, $C_2$-$C_8$, $C_2$-$C_6$, $C_2$-$C_4$) alkynyl groups are intended. Alkynyl groups may contain more than one unsaturated bond. Examples include, but are not limited to, $C_2$-$C_6$-alkynyl, such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, and 1-ethyl-1-methyl-2-propynyl. Alkynyl substituents may be unsubstituted or substituted with one or more chemical moieties. Examples of suitable substituents include, for example, hydroxy, nitro, cyano, formyl, $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkoxycarbonyl, $C_1$-$C_6$ haloalkoxycarbonyl, $C_1$-$C_6$ carbamoyl, $C_1$-$C_6$halocarbamoyl, hydroxycarbonyl, $C_1$-$C_6$ alkylcarbonyl, $C_1$-$C_6$haloalkylcarbonyl, aminocarbonyl, $C_1$-$C_6$ alkylaminocarbonyl, haloalkylaminocarbonyl, $C_1$-$C_6$ dialkylaminocarbonyl, and $C_1$-$C_6$ dihaloalkylaminocarbonyl, provided that the substituents are sterically compatible and the rules of chemical bonding and strain energy are satisfied. Preferred substituents include cyano and $C_1$-$C_6$ alkoxy.

As used herein, the term "aryl," as well as derivative terms such as aryloxy, refers to groups that include a monovalent aromatic carbocyclic group of from 6 to 14 carbon atoms. Aryl groups can include a single ring or multiple condensed rings. In some embodiments, aryl groups include $C_6$-$C_{10}$ aryl groups. Examples of aryl groups include, but are not limited to, phenyl, biphenyl, naphthyl, tetrahydronaphthyl, phenylcyclopropyl, and indanyl. In some embodiments, the aryl group can be a phenyl, indanyl or naphthyl group. The term "heteroaryl", as well as derivative terms such as "heteroaryloxy", refers to a 5- or 6-membered aromatic ring containing one or more heteroatoms, viz., N, O or S; these heteroaromatic rings may be fused to other aromatic systems. The aryl or heteroaryl substituents may be unsubstituted or substituted with one or more chemical moieties. Examples of suitable substituents include, for example, hydroxy, nitro, cyano, formyl, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ acyl, $C_1$-$C_6$ alkylthio, $C_1$-$C_6$ alkylsulfinyl, $C_1$-$C_6$ alkylsulfonyl, $C_1$-$C_6$ alkoxycarbonyl, $C_1$-$C_6$ carbamoyl, hydroxycarbonyl, $C_1$-$C_6$ alkylcarbonyl, aminocarbonyl, $C_1$-$C_6$ alkylaminocarbonyl, $C_1$-$C_6$ dialkylaminocarbonyl, provided that the substituents are sterically compatible and the rules of chemical bonding and strain energy are satisfied. Preferred substituents include halogen, $C_1$-$C_2$ alkyl and $C_1$-$C_2$ haloalkyl.

As used herein, the term "arylalkyl" refers to an alkyl group substituted with an unsubstituted or substituted aryl group. $C_7$-$C_{10}$ arylalkyl refers to a group wherein the total number of carbon atoms in the group is 7 to 10, not including the carbon atoms present in any substituents of the aryl group.

As used herein, alkoxy refers to a group of the formula $R-O-$, where R is alkyl as defined above. Unless otherwise specified, alkoxy groups wherein R is a $C_1$-$C_8$ alkyl group are intended. Examples include methoxy, ethoxy, propoxy, 1-methyl-ethoxy, butoxy, 1-methyl-propoxy, 2-methyl-propoxy, 1,1-dimethyl-ethoxy, pentoxy, 1-methyl-butyloxy, 2-methyl-butoxy, 3-methyl-butoxy, 2,2-di-methyl-propoxy, 1-ethyl-propoxy, hexoxy, 1,1-dimethyl-propoxy, 1,2-dimethyl-propoxy, 1-methyl-pentoxy, 2-methyl-pentoxy, 3-methyl-pentoxy, 4-methyl-penoxy, 1,1-dimethyl-butoxy, 1,2-dimethyl-butoxy, 1,3-dimethyl-butoxy, 2,2-dimethyl-butoxy, 2,3-dimethyl-butoxy, 3,3-dimethyl-butoxy, 1-ethyl-butoxy, 2-ethylbutoxy, 1,1,2-trimethyl-propoxy, 1,2,2-trimethyl-propoxy, 1-ethyl-1-methyl-propoxy, and 1-ethyl-2-methyl-propoxy.

As used herein, haloalkoxy refers to a group of the formula $R-O-$, where R is haloalkyl as defined above. Unless otherwise specified, haloalkoxy groups wherein R is a $C_1$-$C_8$ alkyl group are intended. Examples include chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro,2-difluoroethoxy, 2,2-dichloro-2-fluoroethoxy, 2,2,2-trichloroethoxy, pentafluoroethoxy, and 1,1,1-trifluoroprop-2-oxy.

As used herein, alkylthio refers to a group of the formula R—S— where R is alkyl as defined above. Unless otherwise specified, alkylthio groups wherein R is a $C_1$-$C_8$ alkyl group are intended. Examples include, but are not limited to, methylthio, ethylthio, propylthio, 1-methylethylthio, butylthio, 1-methyl-propylthio, 2-methylpropylthio, 1,1-dimethylethylthio, pentylthio, 1-methylbutylthio, 2-methylbutylthio, 3-methylbutylthio, 2,2-dio-methylpropylthio, 1-ethylpropylthio, hexylthio, 1,1-dimethyl propylthio, 1,2-dimethyl propylthio, 1-methylpentylthio, 2-methylpentylthio, 3-methylpentylthio, 4-methyl-pentylthio, 1,1-dimethyl butylthio, 1,2-dimethyl-butylthio, 1,3-dimethyl-butylthio, 2,2-dimethyl butylthio, 2,3-dimethyl butylthio, 3,3-dimethylbutylthio, 1-ethylbutylthio, 2-ethylbutylthio, 1,1,2-trimethyl propylthio, 1,2,2-trimethyl propylthio, 1-ethyl-1-methyl propylthio, and 1-ethyl-2-methylpropylthio.

As used herein, haloalkylthio refers to an alkylthio group as defined above wherein the carbon atoms are partially or entirely substituted with halogen atoms. Unless otherwise specified, haloalkylthio groups wherein R is a $C_1$-$C_8$ alkyl group are intended. Examples include, but are not limited to, chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2-difluoroethylthio, 2,2-dichloro-2-fluoroethylthio, 2,2,2-trichloroethylthio, pentafluoroethylthio, and 1,1,1-trifluoroprop-2-ylthio.

The terms "isolate," "isolating," or "isolation" as used herein mean to partially or completely remove or separate the desired product from the other components of a finished chemical process mixture using standard methods such as, but not limited to, filtration, extraction, distillation, crystallization, centrifugation, trituration, liquid-liquid phase separation or other methods known to those of ordinary skill in the art. The isolated product may have a purity that ranges from <50% to >50%, and may be purified to a higher purity level using standard purification methods. The isolated product may also be used in a subsequent process step with or without purification.

The term "palladium catalyst" used herein means a molecule or compound generated from a palladium compound and a ligand or a preformed compound containing palladium and a ligand. Examples of palladium compounds include, but are not limited to, palladium(II) acetate ($Pd(OAc)_2$) and palladium(II) chloride ($PdCl_2$). Examples of ligands include, but are not limited to, tri-tert-butylphosphine, tricyclohexylphosphine, di-tert-butylphenylphosphine, dicyclohexylphenylphosphine, triphenylphosphine, tri(o-tolyl)phosphine, 1,2-bis(diphenylphosphino)ethane, 1,3-bis(diphenylphosphaneyl)propane, 1,4-bis(diphenylphosphino)butane, 1,1'-ferrocenediyl-bis(diphenylphosphine) (dppf). Examples of a preformed compound containing palladium and a ligand include, but are not limited to, bis(triphenylphosphine)palladium(II) dichloride, bis(acetato)bis(triphenylphosphine)palladium(II), [1,1'-bis(diphenylphosphino)ferrocene]dichloropalladium(II), [1,1'-bis(di-tert-butylphosphino)ferrocene]dichloropalladium(II), tetrakis(triphenylphosphine)palladium(0), and tris(dibenzylideneacetone)dipalladium(0).

Alkali metal and derivative terms such as alkali metal cation as used herein means any of the elements lithium, sodium, potassium, rubidium, cesium, and francium, occupying Group IA (1) of the periodic table. Alkali metal cations have a +1 charge.

Fluorinating compound or fluorinating mixture of compounds as used herein means a compound capable of installing a fluorine atom on a compound. Examples of fluorinating compounds or fluorinating mixtures of compounds include, but are not limited to, is potassium fluoride, cesium fluoride, tetramethylammonium fluoride, potassium fluoride/tetramethylammonium chloride, cesium fluoride/tetramethylammonium chloride, tetramethylammonium fluoride/tetramethylammonium chloride, or mixtures thereof.

"Acylation catalyst" as used herein means a compound that accelerates the reaction that adds an acyl group (i.e., —C(O)— group to another compound. Examples of acylation catalysts include, but are not limited to, 4-(dimethylamino)pyridine (DMAP), and N-methylimidazole.

"Continuous flow", "flow", "continuous formation", "continuous process", or other derivative terms as used herein means methods that produce a minimum amount of a reactive intermediate at any given time and provide reduced cycle times in comparison to conventional methods. U.S. Pat. No. 9,145,428 B2 (the disclosure of which is explicitly incorporated by reference herein) describes methods and systems using continuous flow.

In the processes described herein the 4-amino-6-(heterocyclic)picolinates of Formula I, wherein R, $W^1$, $W^2$, Y, and Z are as previously defined, may be prepared by reacting a compound of Formula A, wherein R is as previously defined, with a compound of Formula B1 or B2 or mixtures thereof, wherein $R^3$, $R^4$, $W^1$, $W^2$, Y, and Z are as previously defined. Compounds of Formula A may be prepared from 4-amino-3,5,6-trichloropicolinic acid (Picloram), or esters or derivatives thereof.

Formula I

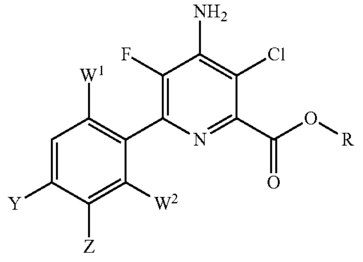

A process for the preparation of compounds of Formula A is depicted in Scheme 2. In one embodiment, 3,5,6-trichloropicolinic acid (Picloram, $C_2$) may be converted to the corresponding ester D2, wherein $Z^1$ is COOR and R is not H, via methods that include, but are not limited to, coupling the acid $C_2$ with an alcohol ROH, wherein R is $C_1$-$C_{12}$ alkyl, $C_3$-$C_{12}$ alkynyl, $C_1$-$C_3$ alkyl substituted with CN, or $C_6$-$C_{12}$ arylalkyl, using any number of suitable activating agents such as those used for peptide couplings including dicyclohexylcarbodiimide (DCC), N-(3-dimethylaminopropyl)-N'-ethylcarbodiimide hydrochloride (EDCI), or carbonyl diimidazole (CDI); forming the acid chloride of $C_2$ by reaction with thionyl chloride or oxalyl chloride in the presence of an alcohol ROH, wherein R is as previously defined; contacting the acid $C_2$ with an alcohol ROH, wherein R is as previously defined, in the presence of an acid; and reacting the compound of Formula $C_2$ with alkylating agents such as substituted or unsubstituted alkyl halides, substituted or unsubstituted arylalkyl halides, or substituted or unsubstituted alkyl sulfonates in the presence of one or more bases such as triethylamine, N,N-diisopropylethylamine, 3,5-lutidine, 2,6-lutidine, 3-methylpyridine, or lithium or potassium carbonate, in a solvent such as tetrahydrofuran, dimethyl sulfoxide, N,N-dimethylformamide, dichloromethane, or 1,2-dichloroethane as in step a of Scheme 2.

The ester D2 ($Z^1$ is COOR, R is not H) or nitrile C1 ($Z^1$ is CN) may be transformed to the corresponding phthalimides, E1 and E2, respectively, wherein A represents the substitution on the phthalimide and is independently selected from H, F, Cl, Br, I, $C_1$-$C_4$ alkyl, $C_1$-$C_4$ alkoxy, $C_1$-$C_4$ haloalkyl, $C_1$-$C_4$ haloalkoxy, and nitro, wherein n is 1, 2, 3, or 4; and $Z^1$ is as previously defined; by reaction with a phthaloyl halide, such as phthaloyl chloride, or phthalic anhydride; optionally a base; optionally an acylation catalyst; a solvent or solvent mixture; at a temperature from ambient temperature to about 100° C. as in step b of Scheme 2. Suitable optional bases include, but are not limited to, trimethylamine, triethylamine, tripropylamine, pyridine, 2-picoline, and 3-picoline. Suitable optional acylation catalysts include, but are not limited to, 4-(dimethylamino) pyridine (DMAP) and N-methylimidazole. Suitable solvents include, but are not limited to, acetonitrile, toluene, N,N-dimethylformamide (DMF), propionitrile, benzonitrile, tetrahydrofuran (THF), 2-methyl-THF, dioxane, cyclopentyl methyl ether (CPME), monoethyleneglycol ethers, diethyleneglycol ethers, monopropyleneglycol ethers or dipropyleneglycol ethers, and methyl isobutyl ketone (MIBK), and mixtures thereof. The temperature range for conducting this step may range from about 25° C. to about 100° C., from about 25° C. to about 90° C., from about 25° C. to about 80° C., from about 25° C. to about 70° C., from about 25° C. to about 60° C., or from about 25° C. to about 55° C., and the reaction may be conducted over a time period ranging from about 1 hour to about 72 hours, from about 1 hour to about 48 hours, from about 1 hour to about 24 hours, from about 1 hour to about 12 hours, from about 1 hour to about 6 hours, from about 2 hours to about 24 hours, from about 4 hours to about 24 hours, from about 2 hours to about 12 hours, or from about 4 hours to about 12 hours.

Phthalimides E1 and E2, wherein A, n, and $Z^1$ are as previously defined, can be converted to the difluorinated compounds F1 and F2 by treatment with a a fluorinating compound or a fluorinating mixture of compounds in the presence of a solvent as shown in step c of Scheme 2. Suitable fluorinating compounds or fluorinating mixture of compounds include, but are not limited to, potassium fluoride (KF), cesium fluoride (CsF), and tetramethylammonium fluoride (TMAF), and mixtures thereof, or a mixture of tetramethylammonium chloride (TMAC) with KF or CsF. Suitable solvents include, but are not limited to, polar aprotic solvents such as acetonitrile, propionitrile, benzonitrile, dimethylsulfoxide (DMSO), DMF, sulfolane, N,N-dimethylacetamide (DMA), 1,1-dimethyl-2-imidazolidinone (DMI), N,N'-diethylpropyleneurea (DMPU), N-methylpyrrolidinone (NMP), THF, 2-methyl-THF, dioxane, monoethyleneglycol ethers, diethyleneglycol ethers, monopropyleneglycol ethers, or dipropyleneglycol ethers, and mixtures thereof. It is generally preferred to conduct this reaction under anhydrous or near-anhydrous conditions. These anhydrous or near-anhydrous conditions may be obtained by prior drying of the reactants and solvents. One way to dry the reactants and/or solvents is by removal by distillation of a portion of the solvent prior to conducting the reaction. Suitable reaction temperatures may be a temperature of at least about 0° C., at least about 10° C., at least about 20° C., at least about 25° C., at least about 30° C., at least about 40° C., at least about 50° C., at least about 60° C., at least about 70° C., at least about 80° C., at least about 90° C., or at least about 100° C. The reaction may be conducted at a temperature of about 0° C. to about 50° C., from about 10° C. to about 50° C., from about 25° C. to about 50° C., from about 15° C. to about 150° C., from about 25° C. to about 150° C., from about 35° C. to about 125° C., from about 45° C. to about 115° C., from about 55° C. to about 110° C., from about 65° C. to about 110° C., from about 75° C. to about 110° C., from about 85° C. to about 110° C., from about 90° C. to about 110° C., from about 50° C. to about 100° C., from about 60° C. to about 100° C., from about 70° C. to about 100° C., from about 25° C. to about 90° C., from about 25° C. to about 80° C., about 25° C. and about 110° C., from about 25° C. to about 70° C., or from about 25° C. to about 60° C. The difluorinated compounds F1 and F2 may be isolated by employing standard isolation and purification techniques.

Compounds F1 and F2, wherein A, n, and $Z^1$ are as previously defined, may be transformed to the 4-amino-6-bromopicolinic acid Formula A1, by treatment with hydrogen bromide or hydrobromic acid (HBr) and water, as in step d of Scheme 2. The conversion involves halogen exchange of the 6-fluoro substituent by the hydrobromic acid to provide a 6-bromo substituent, hydrolysis of the $Z^1$ substituent to a carboxylic acid, and removal of the cyclic imide group by hydrolysis to regenerate the 4-amino substituent. A co-solvent of acetic acid (HOAc) is useful to help facilitate this conversion. The HBr salt of Formula A1 may also form in this reaction. This step may be conducted in two stages, wherein the first step is conducted at lower temperature and/or with no or limited amounts of water to achieve halogen exchange of the 6-fluoro substituent, and the second stage is conducted at higher temperature and/or with more water to achieve hydrolysis of the cyclic imide group and the ester (or cyano substituent). Suitable amounts of water relative to compounds F1 and F2 on a molar basis may range from about 1 to about 30, from about 1 to about 20, from about 1 to about 10, from about 1 to about 8, from about 1 to about 6, from about 1 to about 4, from about 2 to about 5, from about 2 to about 4, or from about 3 to about 4 molar equivalents of water per mole of compounds of Formula F1 and F2. Suitable amounts of hydrobromic acid (HBr) in this step relative to the compounds of Formula F1 and F2 on a molar basis may range from about 50 to about 1, from about 40 to about 1, from about 30 to about 1, from about 20 to about 1, from about 10 to about 1, from about 8 to about 1, from about 6 to about 1, from about 3 to about 1, from about 2 to about 1, or from about 3 to about 2 molar equivalents of HBr per mole of compounds of Formula F1 and F2. The reaction may be conducted at a temperature from about 50° C. to about 150° C., from about 60° C. to about 140° C., from about 70° C. to about 130° C., from about 80° C. to about 120° C., from about 90° C. to about 120° C., or from about 100° C. to about 120° C. Formula A1 may be isolated by employing standard isolation and purification techniques, which may include, but are not limited to, separating possible by-products via solvent extraction with an organic, an aqueous, or an organic-aqueous solvent, or differential aqueous solubility at certain pH levels or ranges. The HBr salt of Formula A1 may be formed in small amounts and be present in the isolated product of Formula A1. This salt may be reduced or removed from Formula A1 by solvent extractions with water or with alcohol-water mixtures such as methanol-water. The compound of Formula A1 may be converted into the ester of Formula A, wherein R is $C_1$-$C_{12}$ alkyl, $C_6$-$C_{12}$ arylalkyl, $C_3$-$C_{12}$ alkynyl or $C_1$-$C_3$ alkyl substituted with CN, via methods that include, but are not limited to, coupling the compound of Formula A1 with an alcohol ROH, wherein R is as previously defined, using any number of suitable activating agents such as those used for peptide couplings including dicyclohexylcarbodiimide (DCC), N-(3-dimethylaminopropyl)-N'-ethylcarbodiimide hydrochloride (EDCI), or carbonyl diimidazole (CDI); contacting the compound of Formula A1 with an alcohol ROH, wherein R is as previously defined, in the presence of an acid; and reacting the compound of Formula A1 with alkylating agents such as substituted or unsubstituted alkyl halides, substituted or unsubstituted alkynyl halides, substituted or unsubstituted arylalkyl halides, or substituted or unsubstituted alkyl sulfonates in the presence of one or more bases such as triethylamine, N,N-diisopropylethylamine, 3,5-lutidine, 2,6-lutidine, 3-methylpyridine, or lithium or potassium carbonate, in a solvent such as tetrahydrofuran, dimethyl sulfoxide, N,N-dimethylformamide, dichloromethane, or 1,2-dichloroethane as in step e of Scheme 2.

In one embodiment, the compound of Formula A may be isolated by employing standard isolation and purification techniques. For example, the reaction mixture product may be isolated using standard methods as known in the art and as described herein, and purified by crystallization or recrystallization using a single solvent or a mixture of two or more solvents. The reaction mixture product may be purified by washing it with or stirring it in a one-, two- or three-component solvent mixture. In one embodiment, the reaction mixture product may be purified by stirring it in an aqueous alcohol solvent mixture which can also be described as an aqueous alcohol slurry treatment. The reaction mixture product of Formula A may also be purified by dissolving it in one solvent to form a solution and then adding a second solvent to the solution to cause the compound of Formula A to crystallize out of the mixture of the two solvents.

In one embodiment, the compound of Formula A may be further treated with another solvent and base without isolation.

Scheme 2

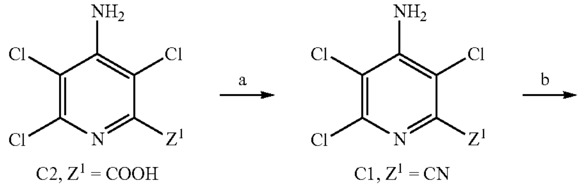

C2, $Z^1$ = COOH

C1, $Z^1$ = CN
D2, $Z^1$ = COOR

-continued

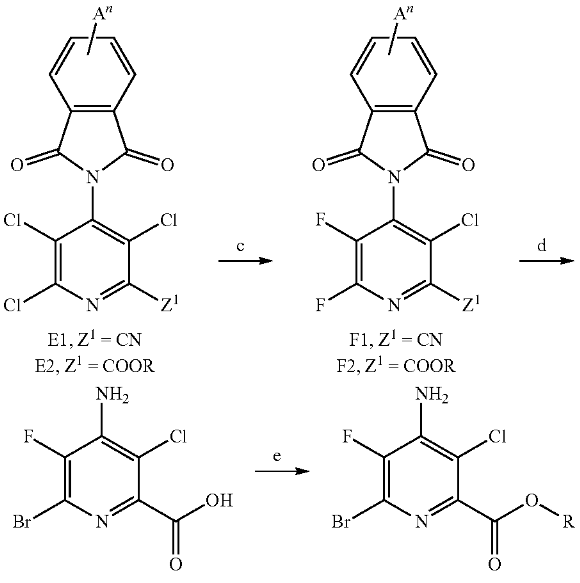

E1, $Z^1$ = CN
E2, $Z^1$ = COOR

F1, $Z^1$ = CN
F2, $Z^1$ = COOR

Formula A1

Formula A

Compounds of Formulae B1 and B2 may be synthesized from compounds of formula G, wherein $R^5$ is a fluorine, and $R^6$, $R^{6'}$, $R^7$, $R^{7'}$, $R^8$, and $R^9$ are H, by reaction with a trialkylsilyl halide, such as chlorotrimethylsilane or tert-butyldimethylsilyl chloride in a polar, aprotic solvent such as THF, and in the presence of a base such as sodium hydride, n-butyllithium, or potassium tert-butoxide to provide the compounds of formula H, wherein $R^8$ is a trialkylsilyl, wherein $R^{10}$ is trimethylsilyl or tert-butyldimethylsilyl and $R^5$, $R^6$, $R^{6'}$, $R^7$, $R^{7'}$, and $R^9$ are as previously defined as in step a of Scheme 3. Depending on the base used, the reactions can be conducted at a temperature from about −78° C. to 0° C. or from about 40° C. to about 55° C. The compounds of formula H, wherein $R^5$ is a fluorine, $R^8$ is a trialkylsilyl, wherein $R^{10}$ is trimethylsilyl or tert-butyldimethylsilyl, and $R^6$, $R^{6'}$, $R^7$, $R^{7'}$, and $R^9$ are H, can be transformed into boronic acids, boronates, or borate salts by ortho-lithiation with sec-butyllithium in a polar, aprotic solvent such as THF at a temperature from about −78° C. to about −10° C., followed by reaction with a borate such as 2-isopropoxy-4,4,5,5-tetramethyl-1,3,2-dioxaborolane, triisopropyl borate, or trimethyl borate. Depending upon the type of manipulation after reaction, such as treatment with aqueous acid or a solvent such as methanol, the compounds of formula B1, wherein $R^9$ is a boronic acid, wherein $R^3$ is H, or boronate, wherein $R^3$ is $C_1$-$C_6$ alkyl, or alternatively two $R^3$ may form a $C_2$-$C_6$ alkyl linkage, which together with B and two O form a 5- to 9-atom cyclic structure, $R^8$ is H or a trialkylsilyl such as tert-butyldimethylsilyl, $R^5$ is a fluorine, and $R^6$, $R^{6'}$, $R^7$, and $R^{7'}$ are H; or the compounds of formula B2, wherein $R^9$ is a borate salt, wherein $R^4$ is a $C_1$-$C_6$ alkyl and $M^+$ is an alkali metal cation; $R^8$ is a trialkylsilyl, wherein $R^{10}$ is tert-butyldimethylsilyl, and $R^6$, $R^{6'}$, $R^7$, and $R^{7'}$ are H, may be isolated.

In one embodiment, any or all of the steps in the synthesis of Formula B1 or B2 may be conducted by batch process. In another embodiment, any or all of the steps in the synthesis of Formula B1 or B2 may be conducted under flow conditions.

Scheme 3

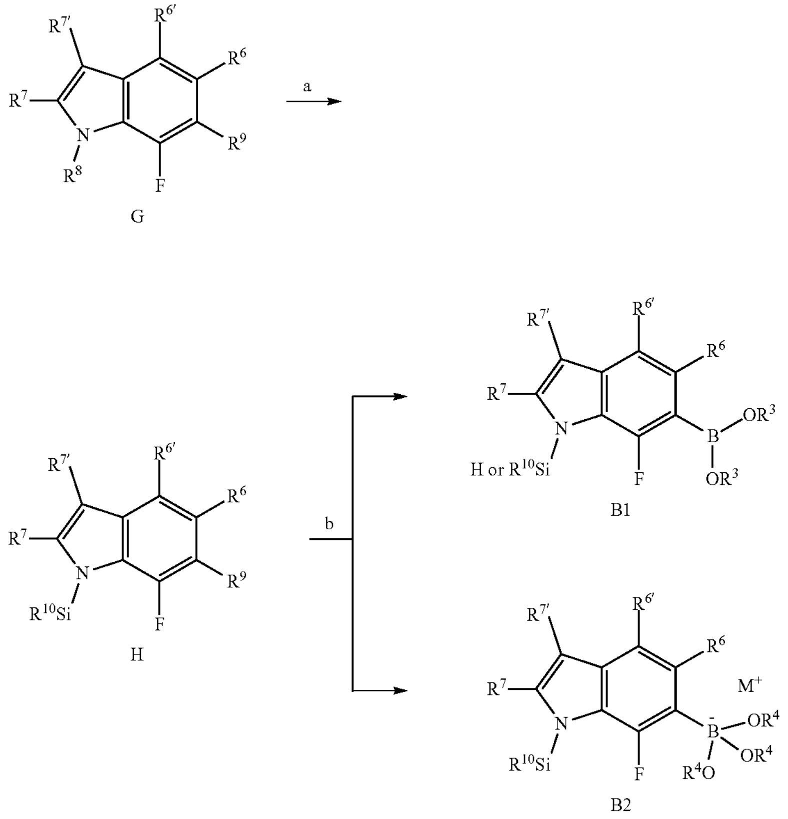

G, H, B1, B2

In one embodiment, compounds of Formula I may be prepared by reaction of the isolated compound of Formula A with a compound of Formula B1 or Formula B2, or mixtures thereof, along with one or more bases, one or more solvents, a palladium catalyst and optionally, a ligand vvas in step a of Scheme 4. The reaction can be conducted at temperatures from about 25° C. to about 100° C. Suitable bases for this reaction include, but are not limited to, potassium carbonate, potassium bicarbonate, sodium carbonate, sodium bicarbonate, potassium acetate, sodium acetate, potassium phosphate monobasic, potassium phosphate dibasic, potassium phosphate tribasic, sodium tetraborate, potassium hydroxide, sodium hydroxide, cesium fluoride, potassium fluoride, triethylamine, triisopropylamine, diisopropylamine, diethylamine, and diisopropylethylamine. Preferred bases include sodium hydroxide, potassium carbonate and potassium bicarbonate. Suitable solvents include, but are not limited to, methyl isobutyl ketone (MIBK), dimethoxyethane (DME), acetonitrile (MeCN), tetrahydrofuran (THF), methanol (MeOH), benzyl alcohol, toluene, water, and mixtures thereof. Suitable ligands for the palladium catalyst system include, but are not limited to, bis(phosphine) ligands, trialkylphosphines and triarylphosphines. These include, but are not limited to, tri-tert-butylphosphine, tricyclohexylphosphine, di-tert-butylphenylphosphine, dicyclohexylphenylphosphine, triphenylphosphine, tri(o-tolyl)phosphine, 1,2-bis(diphenylphosphino)ethane, 1,3-bis (diphenylphosphaneyl)propane, 1,4-bis(diphenylphosphino) butane, 1,1'-ferrocenediyl-bis(diphenylphosphine) (dppf), 4-diphenylphosphinomethyl polystyrene resin crosslinked, sodium diphenylphosphinobenzene-3-sulfonate with 2% DVB, tri(p-tolyl)phosphine, and (±)-2,2'-bis(diphenylphosphino)-1,1'-binaphthyl. The concentration of the ligand can vary. In some embodiments, the concentration of the ligand is from about 0.4% to about 8.0% relative to the limiting reagent, preferably 0.5% to about 6.0%, preferably 0.5% to about 4.0%, preferably 0.5% to about 2%, more preferably about 1.0%. In some embodiments, the ligand is triphenylphosphine ($PPh_3$). Suitable palladium compounds include, but are not limited to, palladium(II) acetate ($Pd(OAc)_2$) and palladium(II) chloride ($PdCl_2$). Suitable palladium catalysts include, but are not limited to, bis(triphenylphosphine)palladium(II) dichloride ($PdCl_2(Ph_3P)_2$), bis (acetato)bis(triphenylphosphine)palladium(II) ($Pd(OAc)_2(Ph_3P)_2$), [1,1'-bis(diphenylphosphino)ferrocene]dichloropalladium(II) ($PdCl_2(dppf)_2$)), [1,1'-bis(di-tert-butylphosphino)ferrocene]dichloropalladium(II) ($PdCl_2$(dtbpf), tetrakis(triphenylphosphine palladium(0) ($Pd(PPh_3)_4$), and tris (dibenzylideneacetone)dipalladium(0) ($Pd_2(dba)_3$)). The concentration of the palladium catalyst can vary. In some embodiments, the concentration is less than 4%, preferably less than 3%, preferably less than 1%. In some embodiments, the concentration of the palladium catalyst is from about 0.1% to about 2.0% relative to the limiting reagent, preferably 0.2% to about 1.0%, more preferably about 0.3%. In some embodiments, the palladium catalyst is palladium (II) acetate and a ligand. In another embodiment, the palladium catalyst is bis(triphenylphosphine)palladium(II) dichloride ($PdCl_2(Ph_3P)_2$). In still another embodiment, the palladium catalyst is [1,1'-bis(di-tert-butylphosphino)ferrocene]dichloropalladium(II) ($PdCl_2$(dtbpf).

Scheme 4

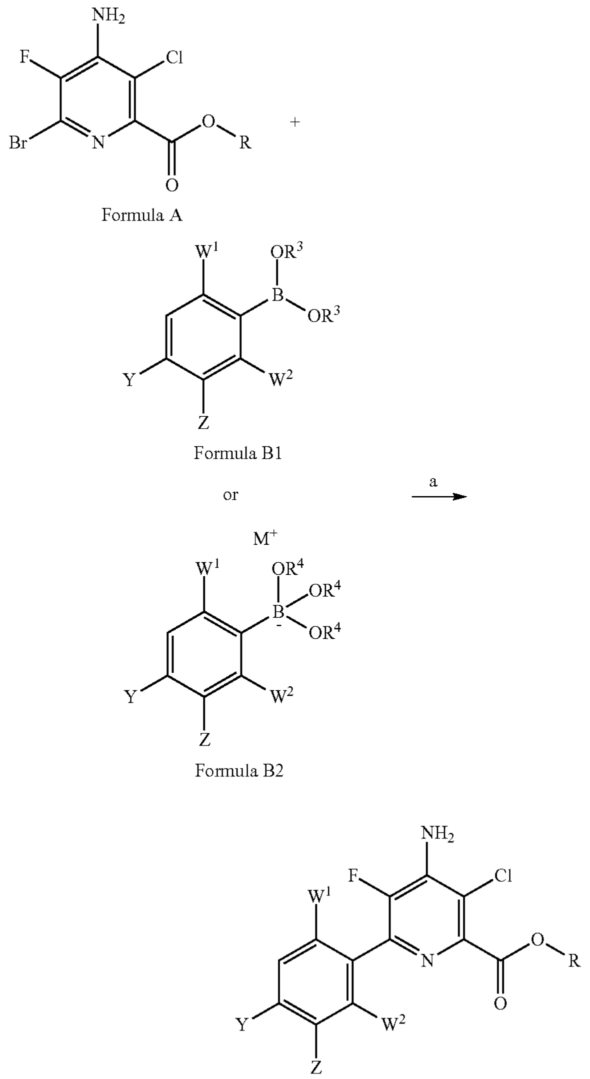

Formula A

Formula B1 or

Formula B2

Formula I

The following examples are presented to illustrate the disclosure.

EXAMPLES

Example 1: Preparation of Methyl 4-amino-3,5,6-trichloropicolinate (1)

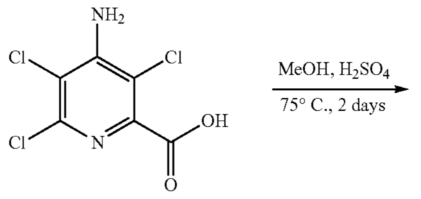

C2

-continued

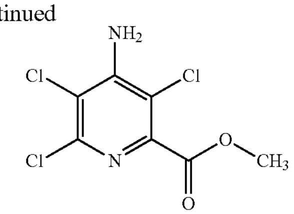

1

4-Amino-3,5,6-trichloropicolinic acid (Picloram, C2; 100 grams (g), 414 millimoles (mmol)) was suspended in methanol (800 milliliters (mL)). Concentrated sulfuric acid (26 mL, 487 mmol) was added slowly at room temperature. The reaction mixture was stirred at 75° C. (oil bath with condenser) for 2 days. The mixture was cooled to room temperature. Water (200 mL) was added. The light brown solution was concentrated to remove the solvent. The resulting residue was dissolved in water (200 mL) and ethyl acetate (EtOAc; 600 mL). The solution was cooled in an ice-bath and neutralized with 4 Normal (N) sodium hydroxide (NaOH) and saturated sodium bicarbonate ($NaHCO_3$) solution to pH=8. The organic layer was separated and the aqueous layer was washed with EtOAc. The combined organic extracts were dried and concentrated to yield the title compound as pale yellow solid (71 g, 67%, high performance liquid chromatography (HPLC) purity 99.9%): mp 125.8-126.1° C.; $^1H$ NMR (400 MHz, $CDCl_3$) δ 5.38 (br s, 2H), 3.97 (s, 3H).

Example 2: Preparation of isopropyl 4-amino-3,5,6-trichloropicolinate (2)

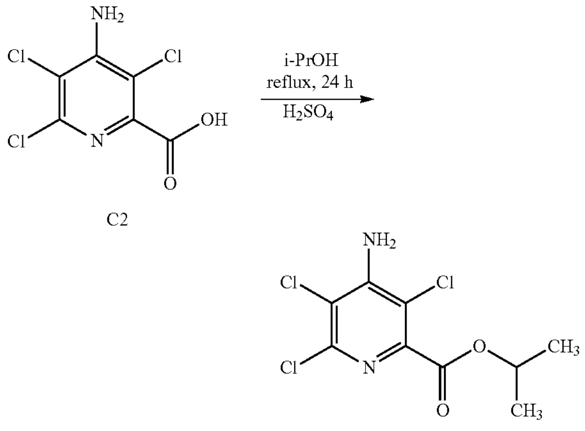

C2

2

Picloram (C2; 4.66 g, 18.3 mmol) was suspended in isopropyl alcohol (30 mL). Concentrated sulfuric acid (0.6 g, 6.1 mmol) was added at room temperature. The reaction mixture was heated at reflux for 18 hours. The reaction mixture was cooled to room temperature. Aqueous potassium carbonate ($K_2CO_3$, 23%; 10 mL) was added slowly to the reaction mixture, and the mixture was stirred for 30 minutes. The reaction mixture was extracted with EtOAc (20 mL) and the organic phase was washed with saturated, aqueous brine (20 mL). The organic phase was dried, and the solvent was evaporated. The residual solid was dried in the vacuum oven to give the title compound as an off-white solid (4.9 g, 94%, HPLC purity 96%): mp 128.5-131.0° C.; 1H NMR (400 MHz, $CDCl_3$) δ 5.35 (br s, 2H), 5.29 (septuplet, J=6.4 Hz, 1H), 1.39 (d, J=6.4 Hz, 6H) ppm.

Example 3: Preparation of Methyl 3,5,6-trichloro-4-(1,3-dioxoisoindolin-2-yl)picolinate (3)

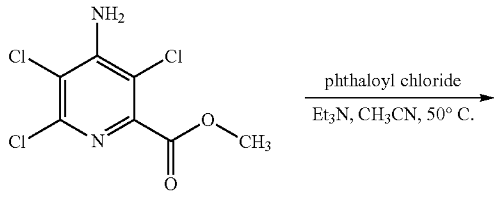

1

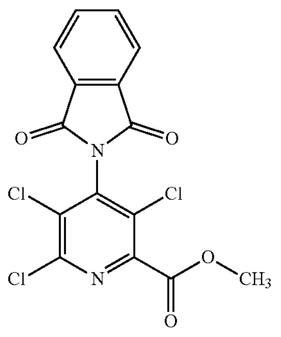

3

Methyl 4-amino-3,5,6-trichloropicolinate (1; 86 g, 337 mmol) was dissolved in acetonitrile (600 mL). Triethylamine (94 mL, 673 mmol) was added at room temperature. Phthaloyl chloride (65 mL, 404 mmol) was added dropwise. The reaction mixture was stirred at 50° C. overnight. Water (100 mL) was added to the mixture. The suspension was stirred for 1 hour and the mixture was filtered through filter paper. The solid was washed with water, then hexane, and dried. The dry solid was suspended in toluene (200 mL), and the resulting mixture was concentrated to provide the title compound as a pale yellow solid (85.1 g, 66%, HPLC purity 97.7%): mp. 185.3-185.9° C.; $^1$H NMR (400 MHz, $CDCl_3$) δ 8.02 (m, 2H), 7.88 (m, 2H), 4.02 (s, 3H).

Example 4: Preparation of 3,5,6-trichloro-4-(1,3-dioxoisoindolin-2-yl)picolinonitrile (4)

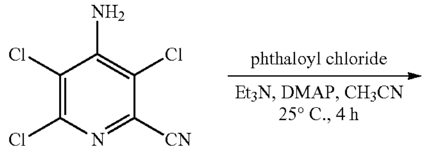

C1

-continued

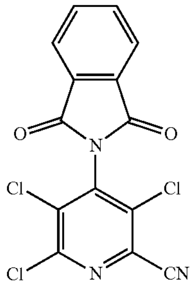

4

4-Amino-3,5,6-trichloropicolinonitrile (C1; 64.1 g, 288 mmol) was suspended in acetonitrile (960 mL). Triethylamine (90 mL, 640 mmol) and 4-(dimethylamino)pyridine (DMAP; 3.52 g, 28.8 mmol) were added at room temperature. Phthaloyl chloride (51.2 mL, 320 mmol) was added slowly, being careful to maintain an internal reaction temperature of less than 50° C. during the addition. The reaction mixture was stirred at room temperature for 4 hours. Water (130 mL) was added to the reaction mixture, and the suspension was stirred for 30 minutes. The solid was collected via filtration and washed with water (4×150 mL) and hexane (2×100 mL). The solid was dried to yield the title compound as a light purple solid (97.0 g, 96%), which was dissolved in dichloromethane and passed through a silica gel pad to give an off-white solid with an HPLC purity of 99.6%: mp 233.7-234.8° C.; $^1$H NMR (400 MHz, DMSO-$d_6$) δ 8.14 (m, 2H), 8.04 (m, 2H).

Example 5A: Preparation of Methyl 3,5,6-trichloro-4-(1,3-dioxoisoindolin-2-yl)picolinate (3)

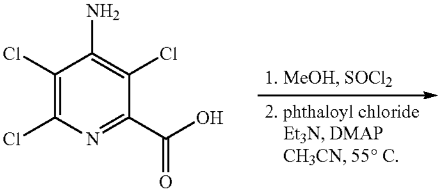

C2

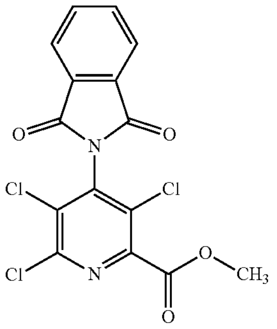

3

Picloram (C2; 105.3 g, 415 mmol) was suspended in MeOH (650 mL) in a 3-Liter (L), three-neck flask equipped with mechanical stirrer and condenser. The mixture was stirred vigorously at room temperature. Thionyl chloride (0.90 mL, 12 mmol) was added dropwise. The reaction mixture was stirred at 75° C. (external temperature) for 18 hours. The methanol was concentrated (about 150 mL remaining). Toluene (500 mL) was added and co-evaporated at 40-55° C. under house vacuum to dryness. Acetonitrile (690 mL), triethylamine (134 mL, 959 mmol), and DMAP (5.33 g, 43.6 mmol) were added. Phthaloyl chloride (77 mL, 480 mmol) was added dropwise, being careful to maintain an internal reaction temperature of less than 55° C. during the addition. After addition was complete, the reaction mixture was stirred for another 2 hours. Water (200 mL) was added to the mixture. The resulting suspension was stirred for 30 minutes and filtered. The wet cake collected on the funnel was washed with water (2×200 mL), hexanes (200 mL) and dried under vacuum. The title compound was isolated as a beige solid (154.4 g, 96% over 2 steps, HPLC purity 98%).

Example 5B: Preparation of Ethyl 3,5,6-trichloro-4-(1,3-dioxoisoindolin-2-yl)picolinate (8)

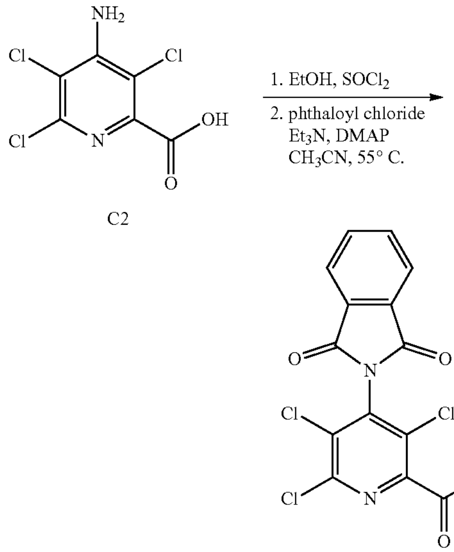

C2

8

A 500 mL round bottom flask was charged with Picloram (C2; 30 g, 122 mmol) and EtOH (200 mL). Thionyl chloride (0.43 mL, 6.1 mmol) was added dropwise. The white slurry was stirred at 75° C. for 6 hours. Additional thionyl chloride (0.43 mL, 6.1 mmol) was added. The reaction mixture was stirred at 75° C. for 16 hours. The reaction mixture was concentrated to yield yellow oil, which was co-evaporated with acetonitrile (2×200 mL) to dryness to give a white solid. The white solid was dissolved in acetonitrile (200 mL). Triethylamine (37.4 mL, 268 mmol), DMAP (1.47 g, 12.2 mmol), and phthaloyl chloride (19.3 mL, 134 mmol) were added sequentially. The temperature was lower than 58° C. during the addition. The reaction mixture was stirred at room temperature for 2 hours, quenched with water (60 mL), and filtered. The filtrate was washed with water and hexanes and dried to provide the title compound (43.3 g, 89%, HPLC purity 99%): 1H NMR (400 MHz, $CDCl_3$) 8.10 (m, 2H), 7.87 (m, 2H), 4.47 (q, J=7.2 Hz, 2H), 1.43 (t, J=7.2 Hz, 3H).

Example 6: Preparation of Isopropyl 3,5,6-trichloro-4-(1,3-dioxoisoindolin-2-yl)picolinate (5)

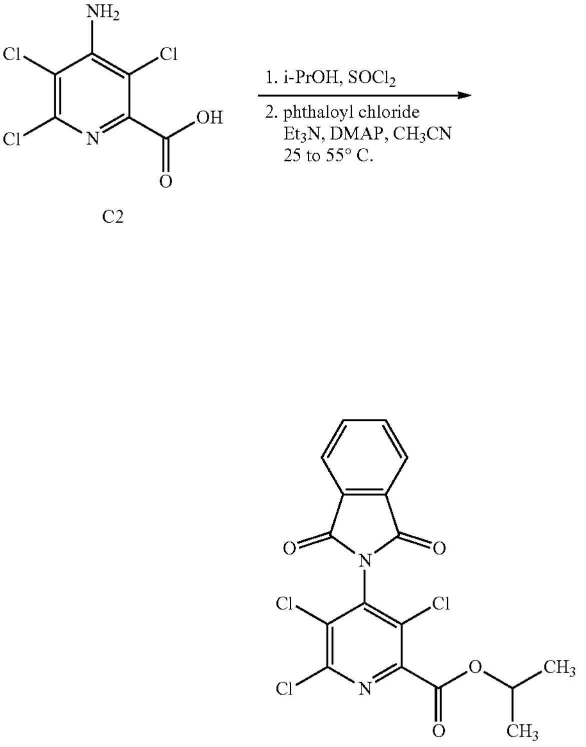

C2

5

Step 1: A 3-L, three-neck flask equipped with mechanical stirrer, condenser, and addition funnel was charged with Picloram (C2; 100 g, 414 mmol) and isopropyl alcohol (950 mL). Thionyl chloride (15.1 mL, 207 mmol) was added to the slurry dropwise via addition funnel at room temperature, and the reaction mixture was heated at reflux for 24 h. The reaction mixture was cooled to room temperature and concentrated to dryness. The residue was co-evaporated with acetonitrile (2×100 mL) to yield a white solid (117.5 g), which is a mixture of 2 (93.6%) and Picloram (2.84%) by HPLC.

Step 2: A 3-L, three-neck flask equipped with mechanical stirrer, thermometer, and addition funnel was charged with the white solid isolated above, acetonitrile (700 mL), triethylamine (150 mL, 1.077 moles (mol)) and DMAP (5.05 g, 41.4 mmol). Phthaloyl chloride (90%; 73 mL, 456 mmol) was added dropwise via addition funnel to maintain the temperature below 55° C. The reaction mixture was stirred at room temperature for 3 hours. Water (250 mL) was added to the mixture. The resulting suspension was stirred for 30 minutes and filtered through filter paper. The solid was washed with water (3×100 mL) and hexane (2×100 mL) and dried. The solid was co-evaporated with toluene (2×250 mL), dried, washed with hexanes (2×200 mL) and dried again. The title compound was isolated as a pale, yellow solid ((151.5 g, 88%, HPLC purity 98.8%): mp 157.0-157.9° C.; $^1H$ NMR (400 MHz, $CDCl_3$) δ 8.04-8.00 (m, 2H), 7.90-7.86 (m, 2H), 5.33 (septuplet, J=6.4 Hz, 1H), 1.42 (d, J=6.4 Hz, 6H).

Example 7: Preparation of isopropyl 3,5,6-trichloro-4-(1,3-dioxoisoindolin-2-yl)picolinate (5)

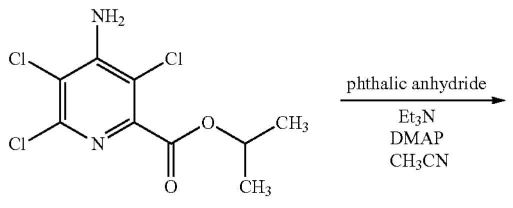

2

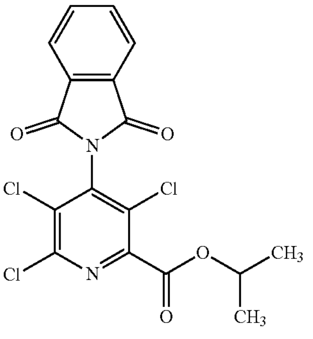

5

Compound 2 (8.1 g, 27.6 mmol) was suspended in acetonitrile (33 mL) in a 100 mL round bottom flask equipped with a magnetic stirrer and a condenser. Triethylamine (9.6 mL, 69.0 mmol) and phthalic anhydride (4.9 g, 33.1 mmol) were added at room temperature. DMAP (0.34 g, 2.76 mmol) was then added. The yellow suspension was stirred at 80° C. (oil bath temperature) for 2 hours. Additional phthalic anhydride (4.0 g, 27.0 mmol) was added to the reaction mixture at 80° C. The reaction mixture was stirred at 80° C. for another 4.5 hours. (Total reaction time was 6.5 hours.) The reaction mixture was cooled to room temperature, and water (33 mL) was added to the mixture. The suspension was stirred for 30 minutes and filtered through filter paper. The wet solid was washed with water and hexane and dried at 55° C. in a vacuum oven. The title compound was isolated as a yellow solid (9.8 g, 86%, HPLC purity 99.2%).

Example 8: Preparation of Isopropyl 3,5,6-trichloro-4-(1,3-dioxoisoindolin-2-yl)picolinate (5)

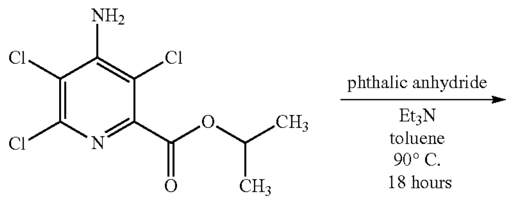

2

-continued

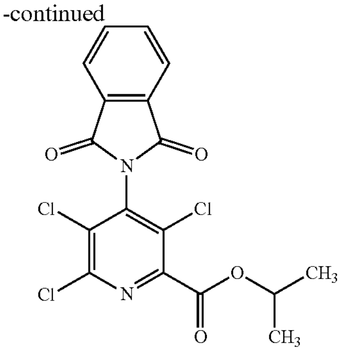

5

To a suspension of compound 2 (2.5 g, 8.82 mmol) in toluene (11 mL) were added triethylamine (2.96 mL, 21.2 mmol) and phthalic anhydride (3.26 g, 22.0 mmol). The resulting suspension was stirred in a 90° C. oil bath for 18 hours. The clear yellow solution was cooled gradually to room temperature to provide a thick beige slurry. Saturated sodium bicarbonate solution (5 mL) was added slowly at room temperature, and the resulting slurry was stirred in an ice-water bath for 1 hour. The solid was collected by vacuum filtration and was washed with water (2×5 mL). The wet solid was dried in a vacuum oven at 55° C. for 5 hours. The title compound was isolated as an off-white powdery solid (3.1 g, 86%, HPLC purity 99.5%).

Example 9: Preparation of isopropyl 3,5,6-trichloro-4-(1,3-dioxoisoindolin-2-yl)picolinate (5)

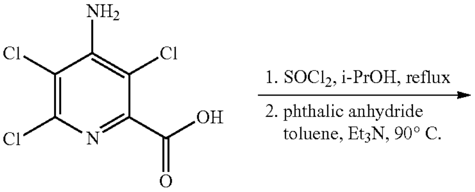

C2

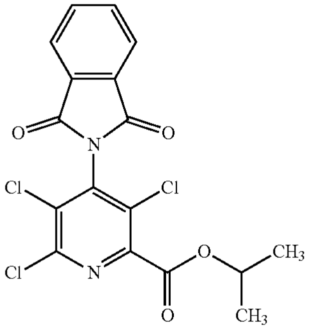

5

A 2-L flask was charged with Picloram (C2; 101.8 g, 98.2% purity, 0.414 mol) and isopropyl alcohol (918.3 mL). Thionyl chloride (15.6 mL, 97% purity, 0.21 mol) was added, and the reaction mixture was heated at reflux for 17 hours. The isopropyl alcohol (750 mL) was distilled off under atmospheric pressure. Toluene (600 mL) was added to the resulting solution. Distillation was continued, and after another 2 hours, a mixture of isopropyl alcohol/toluene (600 mL) was distilled off at 81-110° C. To the stirred suspension were added sequentially triethylamine (144.3 mL, 1.04 mol) and phthalic anhydride (153.3 g, 1.04 mol) in portions. The reaction mixture was heated at 88-93° C. for 17 hours and cooled to room temperature. Saturated aqueous sodium bicarbonate (400 mL) was added slowly over 0.5 hours with cooling to keep the temperature below 20° C. The resultant slurry was stirred at room temperature for 2 hours and filtered. The solid was washed with water (3×100 mL) and dried at 60° C. for 24 h to afford the title compound (144 g, 84%, HPLC purity 99%).

Example 10: Preparation of cyclohexyl 3,5,6-trichloro-4-(1,3-dioxoisoindolin-2-yl)picolinate (10)

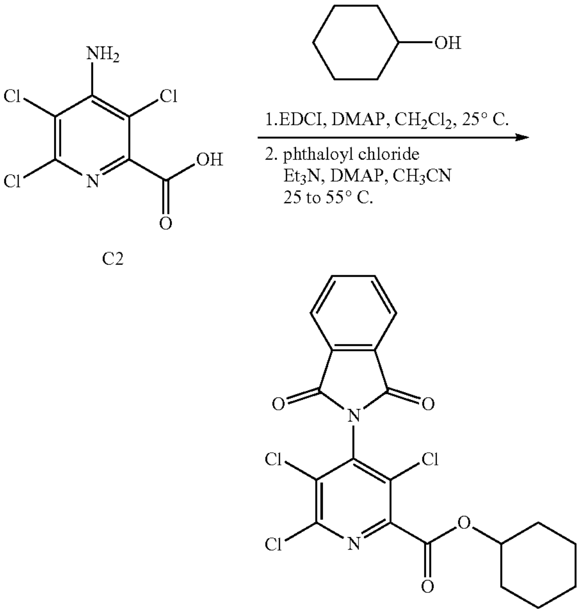

C2

10

Step 1: To a mixture of Picloram (C2; 20 g, 82.8 mmol), DMAP (5.06 g, 41.4 mmol), and hexanol (7.88 g, 78.7 mmol) in dichloromethane (200 mL) was added N-(3-dimethylaminopropyl)-N'-ethylcarbodiimide hydrochloride (EDCI; 17.5 g, 91.1 mmol) in four portions. The white slurry was stirred at room temperature for 16 hours, filtered through a silica pad directly, and washed with dichloromethane (3 L). The product fraction was combined to yield the ester (16.2 g, 60%).

Step 2: To a mixture of the ester from Step 1 (16.2 g, 50.1 mmol), DMAP (0.61 g, 5.01 mmol), and triethylamine (15.4 mL, 110 mmol) in acetonitrile (100 mL) was added phthaloyl chloride (7.9 mL, 55.1 mmol) slowly. The yellow suspension was stirred vigorously for 2 hours, quenched with water (100 mL), filtered and washed with methanol. The solid was co-evaporated with toluene, filtered, and washed with hexanes to give compound the title compound (12.9 g, 57%, HPLC purity 99.1%): $^{1}$H NMR (400 MHz, $CDCl_3$) 8.01 (m, 2H), 7.88 (m, 2H), 5.11 (m, 1H), 2.02 (m, 2H), 1.79 (m, 2H), 1.64 (m, 3H), 1.40 (m, 2H), 1.33 (m, 1H).

Example 11: Preparation of methyl 3-chloro-4-(1,3-dioxoisoindolin-2-yl)-5,6-difluoropicolinate (6)

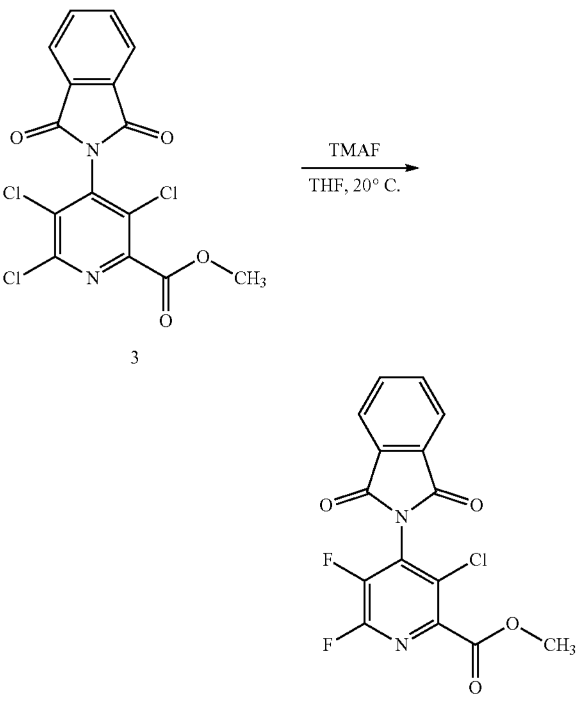

3

6

To compound 3 (5.00 g, 13.0 mmol) in a 250 mL round-bottom flask under nitrogen were added anhydrous tetrahydrofuran (THF; 100 mL) and tetramethylammonium fluoride (TMAF, Aldrich; 4.83 g, 51.87 mmol) in one portion. The reaction mixture was stirred at room temperature for 5 hours, cooled to 0° C., quenched with water (400 mL) and stirred at 0° C. for 1 hour. The solid was collected by filtration, washed with water (2×100 mL) and hexanes (3×100 mL), and dried. The title compound was isolated as a pale yellow solid (4.0 g, 87%, HPLC purity 92.3%): mp 180.2-182.6° C.; 1H NMR (DMSO-$d_6$) δ 8.12 (d, 2H), 8.02 (d, 2H), 3.94 (s, 3H); $^{19}$F NMR δ −83.30, −133.05. Also contained 6.6% of the 3,5,6-trifluorinated side-product.

Example 12: Preparation of Methyl 3-chloro-4-(1,3-dioxoisoindolin-2-yl)-5,6-difluoropicolinate (6)

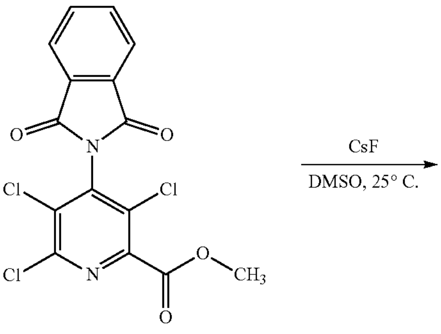

3

-continued

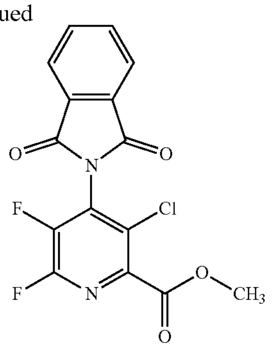

6

-continued

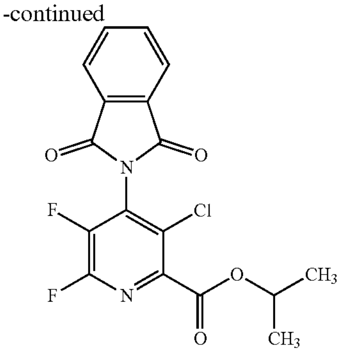

7

A mixture of cesium fluoride (CsF; 82.7 g, 545 mmol) in dimethyl sulfoxide (DMSO; 1.2 L) was distilled at 90° C. under house vacuum to remove DMSO (250 mL). After cooling to room temperature under nitrogen ($N_2$), compound 3 (60.0 g, 156 mmol) was added in three portions. The mixture was stirred vigorously under $N_2$ for 27 hours at 25° C., poured into ice water (3.6 L), stirred for 1 hour, and filtered. The filtered solid washed with water (600 mL) and hexanes (300 mL), and dried to provide the title compound as an off-white solid (55 g, 100% (not purified), HPLC purity 93.6% (also containing 1.3% monofluoro side-product and 2.3% trifluoro side-product). The off-white solid was stirred at reflux in methanol (150 mL) for 30 minutes and filtered to give the title compound as a pale, beige solid (51.1 g, 92.7% yield, HPLC purity 95.7% (also containing 1.3% 6-monofluoro side-product and 1.7% 3,5,6-trifluoro side-product).

A sample of the pale, beige solid from above (1.0 g) was dissolved in a minimum amount of hot ethyl acetate (12.5 mL), and the resulting solution was diluted with methanol (25 mL). The resulting solution was gradually cooled with stirring to room temperature and then was cooled in an ice-water bath. The mixture that formed was filtered, and the filtered solid was washed twice with methanol (5 mL) and dried. The title compound was isolated as off-white, fine crystals (0.81 g, 81% recovery, HPLC purity 98.1%, also containing 0.8% 6-monofluoro side-product and 0.9% 3,5,6-trifluoro side-product.

Example 13: Preparation of Isopropyl 3-chloro-4-(1,3-dioxoisoindolin-2-yl)-5,6-difluoropicolinate (7)

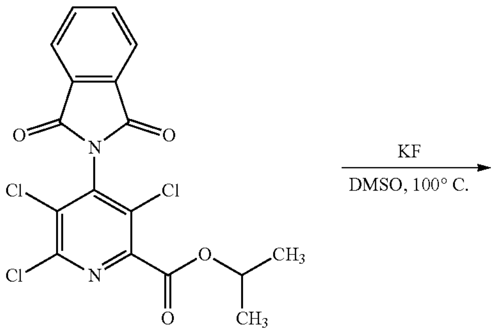

5

Solid potassium fluoride (KF, Sigma Aldrich; 12.7 g, 219 mmol) was added to a 1-L jacketed glass reactor which had been purged with nitrogen and was maintained under an atmosphere of nitrogen. The reactor was fitted with a 1-inch diameter, trayed distilling column. DMSO (Fisher Scientific; 353.0 g) was added to the reactor. The mixture was agitated at a rate of 350 revolutions per minute (RPM). A vacuum of approximately 40 millimeters of mercury (mmHg) was applied and the temperature of the reactor contents was increased to approximately 108° C. Approximately 100 mL of material was distilled with the distilling column and removed from the reactor. The temperature of the reactor contents was reduced to 75° C., and the water content was determined by Karl Fischer analysis to be 51 parts per million (ppm). The reactor was charged with compound 5 (24.9 g, 60.2 mmol) and the temperature was increased to 100° C. The reaction was held at 100° C. for approximately 7.5 hours. The reactor was cooled to 75° C. and the reaction mixture was passed through a fritted filter to remove the solid. The filtered salts were washed with DMSO (44 g), and the filtrate and wash were added to a second vessel for crystallization. The second vessel was cooled to 12° C., the contents were agitated at 250 RPM, and water (363 g) was added continuously to the second vessel over approximately 2 hours. A mixture formed and was stirred for an additional hour at 12° C. The solid was collected by filtration, washed with water (about 68 g), and dried in a vacuum oven at 60° C. (25 torr) overnight. The resulting dry solid (21.5 g, 94%) provided 93.7% of the title compound, 2.6% of the 3,5,6-trifluoro side-product, and 2.0% of the 6-monofluoro side-product: mp 115.8-117.1° C.; 1H NMR (400 MHz, $CDCl_3$) δ 8.00-8.06 (m, 2H), 7.91-7.86 (m, 2H), 5.32 (septet, J=6.0 Hz, 1H), 1.42 (d, J=6.0 Hz, 6H); $^{19}F$ NMR (376 MHz, $CDCl_3$) δ −134.21 (d), −82.76 (d).

Example 14: Preparation of Isopropyl 3-chloro-4-(1,3-dioxoisoindolin-2-yl)-5,6-difluoropicolinate (7)

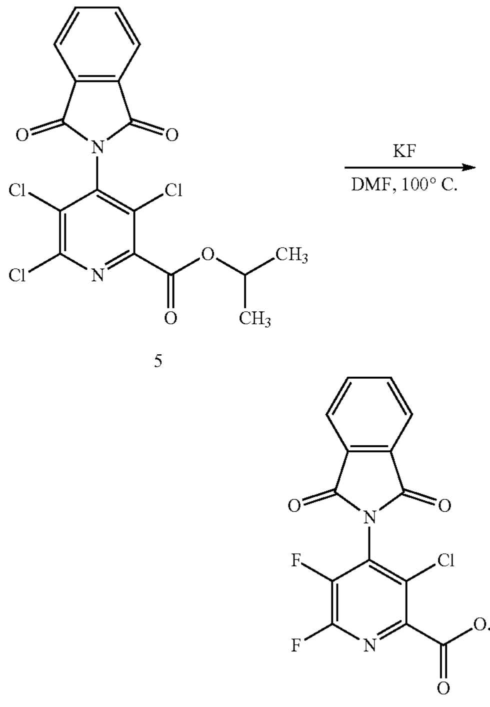

5

7

Solid potassium fluoride (Sigma Aldrich; 7.68 g, 132 mmol) was added to a 1-L jacketed glass reactor which had been purged with nitrogen and was maintained under an atmosphere of nitrogen. The reactor was fitted with a 1-inch diameter, trayed distilling column containing 7 trays. DMF (Fisher Scientific, 211.7 g) and toluene (Fisher Scientific, 41.6 g) were added sequentially to the reactor. The solution was agitated at a rate of 275 RPM. A vacuum of approximately 350 mmHg was applied, and the temperature of the reactor contents was increased to approximately 110° C. Approximately 75 mL of material was distilled with the distilling column and removed from the reactor by decreasing the pressure as material was distilled overhead. The temperature of the reactor contents was reduced to 45° C., and the water content was determined by Karl Fischer analysis to be 101 ppm. The reactor was charged with compound 5 (15.2 g, 36.7 mmol), and the temperature was increased to 100° C. The reaction was held at 100° C. for approximately 33 hours. The reactor was cooled to 40° C. and the reaction mixture was passed through a fritted filter to remove the solids. The filtered salts were washed with DMF (36.1 g) and the filtrate and wash were added to a second vessel for crystallization. The second vessel was cooled to 10° C., the contents were agitated at 250 RPM, and water (170 g) was added continuously over approximately 2 hours. A mixture formed and was stirred for another 4 hours at 10° C. The solid was collected by filtration, washed with water (about 44 g), and dried in a vacuum oven at 60° C. (25 torr) overnight. The resulting dry solid (12.0 g, 80%) provided 82.6% of the title compound, 1.1% of the 3,5,6-trifluoro side-product, and 16.6% of the 6-monofluoro side-product.

Example 15: Preparation of Isopropyl 3-chloro-4-(1,3-dioxoisoindolin-2-yl)-5,6-difluoropicolinate (7)

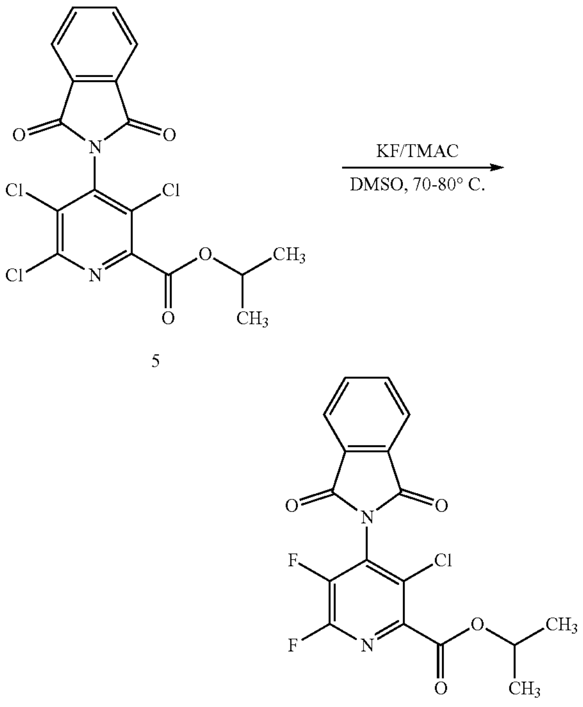

5

7

Solid potassium fluoride (Sigma Aldrich; 11.2 g, 192 mmol) was added to a 1-L jacketed glass reactor which had been purged with nitrogen and was maintained under an atmosphere of nitrogen. The reactor was fitted with a 1-inch diameter, trayed distilling column containing 7 trays. DMSO (Fisher Scientific; 207.2 g) and solid tetramethylammonium chloride (TMAC, Sigma Aldrich; 5.29 g, 48.3 mmol) were added sequentially to the reactor. The mixture was agitated at a rate of 350 RPM. A vacuum of approximately 100 mmHg was applied, and the temperature of the reactor contents was increased to approximately 100° C. Approximately 35 mL of material was distilled with the distilling column and removed from the reactor. The temperature of the reactor contents was reduced to 45° C., and the water content was determined by Karl Fischer analysis to be 102 ppm. The reactor was charged with compound 5 (19.8 g, 47.9 mmol), and the temperature of the reaction mixture was increased to 60° C. The reaction was held at 60° C. for approximately 3.5 hours and then was increased to 70° C. That temperature was held for approximately 8.5 hours at 70° C. and was increased and held for one hour at 80° C. The reactor was cooled to 75° C. and the reaction mixture was passed through a fritted filter to remove the solids. The filtered salts were washed with DMSO (50 g) and the filtrate and wash were added to a second vessel for crystallization. The second vessel was cooled to 21° C., the contents were agitated at 250 RPM, and water (267 g) was added continuously over approximately 2 hours. A mixture formed and was stirred for another one hour at 21° C., and the solid present was then collected by filtration, washed with water (about 66 g), and dried in a vacuum oven at 60° C. (25 torr) overnight. The resulting dry solid (15.5 g, 85% yield)

provided 97.5% of the title compound, which also contained 1.7% of the 3,5,6-trifluoro side-product and 1.9% of the 6-monofluoro side-product.

Example 16: Preparation of Isopropyl 3-chloro-4-(1,3-dioxoisoindolin-2-yl)-5,6-difluoropicolinate (7)

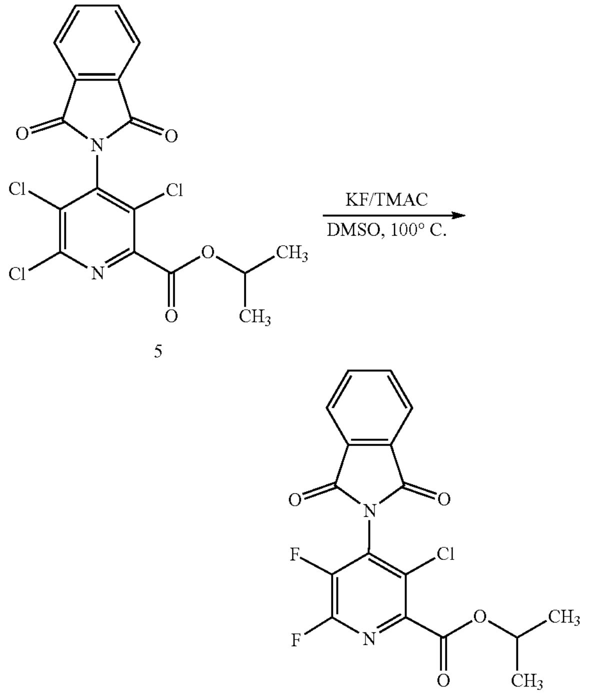

5

7

Solid potassium fluoride (Sigma Aldrich; 12.7 g, 219 mmol) was added to a 1-L jacketed glass reactor which had been purged with nitrogen and was maintained under an atmosphere of nitrogen. The reactor was fitted with a 1-inch diameter, trayed distilling column containing 7 trays. DMSO (Fisher Scientific; 408.9 g) and a solution of 35% tetramethylammonium chloride (TMAC) in methanol (SAChem; 34.6 g, 110 mmol) were added sequentially to the reactor. The mixture was agitated at a rate of 350 RPM. A vacuum of approximately 60 mmHg was applied, and the temperature of the reactor contents was increased to approximately 100° C. Approximately 115 mL of material was distilled with the distilling column and removed from the reactor. The temperature of the reactor contents was reduced to 70° C. and more DMSO (54 g) was added to the reaction mixture before restarting the distillation and collecting approximately 35 mL of additional distillate. The temperature of the reactor contents was reduced to 75° C., and the water content was determined by Karl Fischer analysis to be 179 ppm. The reactor was charged with compound 5 (24.9 g, 60.2 mmol), and the temperature was increased to 100° C. The reaction was held at 100° C. for approximately 2.25 hours. The reactor was cooled to 75° C. and the reaction mixture was passed through a fritted filter to remove the solids. The filtered salts were washed with DMSO (116 g) and the filtrate and wash were added to a second vessel for crystallization. The second vessel was cooled to 14° C., the contents were agitated at 250 RPM, and water (283 g) was added continuously over approximately 2 hours. A mixture formed and was stirred for an additonal hour at 14° C. The solid was collected by filtration, washed with water (about 64 g), and dried in a vacuum oven at 60° C. (25 torr) overnight. The resulting dry solid (22.5 g, 98%) provided 98.3% of the title compound, 3.8% of the 3,5,6-trifluoro side-product, and 0.5% of the 6-monofluoro side-product.

Example 17: Preparation of Ethyl 3-chloro-4-(1,3-dioxoisoindolin-2-yl)-5,6-difluoropicolinate (9)

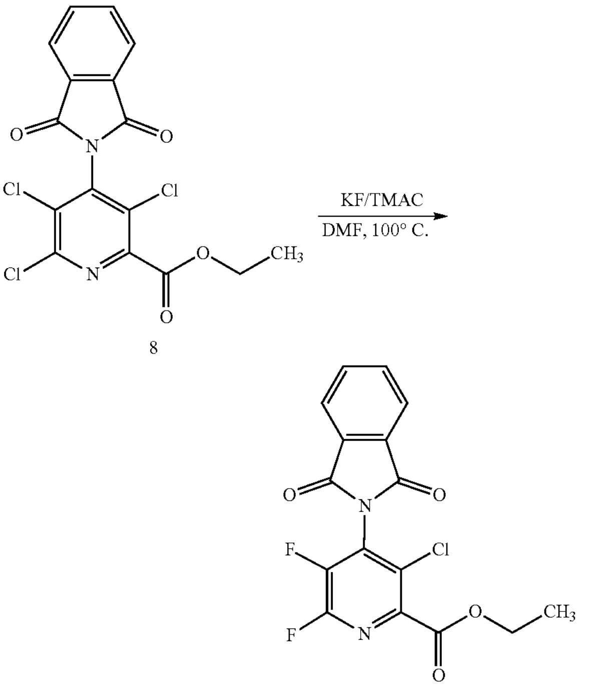

8

9

Solid potassium fluoride (Sigma Aldrich; 5.9 g, 102 mmol; Sigma Aldrich) was added to a 1-L jacketed glass reactor which had been purged with nitrogen and was maintained under an atmosphere of nitrogen. The reactor was fitted with a 1-inch diameter, trayed distilling column containing 7 trays. DMF (Fisher Scientific; 139.5 g) and a solution of 35% tetramethylammonium chloride (TMAC) in methanol (SAChem; 15.8 g, 50.4 mmol) were added sequentially to the reactor. The solution was agitated at a rate of 350 RPM. A vacuum of approximately 90 mmHg was applied, and the temperature of the reactor contents was increased to approximately 90° C. Approximately 75 mL of material was distilled with the distilling column and removed from the reactor. The temperature of the reactor contents was reduced to 45° C., and the water content was determined by Karl Fischer analysis to be 105 ppm. The reactor was charged with compound 8 (10.1 g, 25.1 mmol), and the temperature was increased to 100° C. The reaction was held at 100° C. for approximately 4 hours. The reactor was cooled to 50° C. and the reaction mixture was passed through a fritted filter to remove the solids. The filtered salts were washed with DMF (73 g) and the filtrate and wash were added to a second vessel for crystallization. The second vessel was cooled to 2° C., the contents were agitated at 250 RPM, and water (172.3 g) was added continuously to the reaction mixture over approximately 2 hours in order to keep the temperature of the mixture below 10° C. A mixture formed and was stirred for an additional hour at about 10° C. The solid was collected by filtration, washed with water (about 35 g), and dried in a vacuum oven at 60° C. (25 torr) overnight. The resulting dry solid (6.44 g, 70%) provided 97.3% of the title compound, 2.4% of the 3,5,6-trifluoro side-product and 3.8% of the 6-monofluoro side-product: mp 111.2-116.7° C.; 1-H NMR (400 MHz, $CDCl_3$) δ 8.04-8.00 (m, 2H), 7.90-7.88 (m, 2H), 4.47 (q, J=6.8 Hz, 2H), 1.43 (d, J=6.8 Hz, 3H); $^{19}F$ NMR (376 MHz, $CDCl_3$) −133.57 (d), −82.54 (d).

Example 18: Preparation of Cyclohexyl 3-chloro-4-(1,3-dioxoisoindolin-2-yl)-5,6-difluoropicolinate (11)

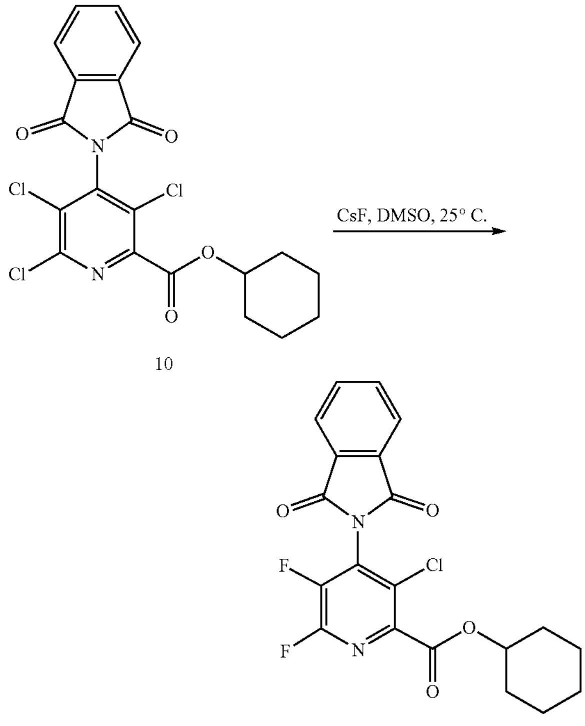

10

11

Cesium fluoride (1.17 g, 7.70 mmol) was added to a 50-mL round bottom flask equipped with stirring bar and distillation apparatus. DMSO (25 mL) was added. The flask was placed in an oil bath, and a vacuum (approximately 1 mm Hg) was applied to the system. DMSO (approximately 10 mL) was distilled. The distillation apparatus was removed and the system was cooled under a nitrogen balloon. When the oil bath reached 25° C., compound 10 (1.0 g, 2.17 mmol) was added in one portion. The reaction mixture was stirred at room temperature under a nitrogen atmosphere for 24 hours, poured into 50 mL ice-water, and stirred for 30 minutes. The product was collected, and the wet cake was washed with water (2×10 mL) and hexane (10 mL) and dried in a vacuum oven at 55° C. The title compound was isolated as a yellow solid (0.89 g, 95%, HPLC purity 92.9%): $^{19}F$ NMR (376 MHz, DMSO-$d_6$) δ −83.3 (d, J=26.7 Hz), −133.7 (d, J=26.7 Hz). Also contained 2.1% of the 3,5,6-trifluoro side-product.

Example 19: Preparation of 4-amino-3,6-dichloro-5-fluoropicolinic acid (12)

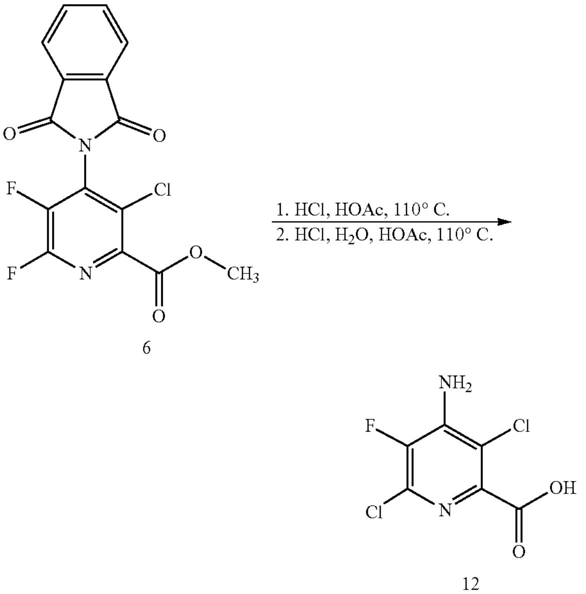 [SMILES: COC(=O)c1nc(F)c(F)c(N2C(=O)c3ccccc3C2=O)c1Cl ; Nc1c(F)c(Cl)nc(C(=O)O)c1Cl]

6

12

Compound 6 (5.0 g, 14.2 mmol) was suspended in a solution of hydrogen chloride (HCl) in acetic acid (HOAc, 2 M; 35.5 mL, 71 mmol) in a 450 mL sealed flask. The mixture was stirred at 110° C. (oil bath) overnight and was cooled to 5° C. Aqueous HCl (12 N, 10 mL) was added slowly to the flask; the flask was sealed again and put into a 110° C. oil bath overnight. The resulting mixture was cooled to 5° C. and filtered. The collected solid was suspended in 2 N aqueous HCl solution (100 mL), stirred at 110° C. for 60 minutes, and filtered. The filtered solid was washed with hexane and dried. The title compound was isolated as an off-white solid (1.88 g, 51%, HPLC purity 97.1%): mp: 211.0-212.7° C.; 1H NMR (DMSO-$d_6$) δ 13.81 (br s, 1H), 7.21 (br s, 2H); $^{19}F$ NMR (DMSO-$d_6$) δ −137.05.

Example 20: Preparation of 4-amino-6-bromo-3-chloro-5-fluoropicolinic Acid (Formula A1)

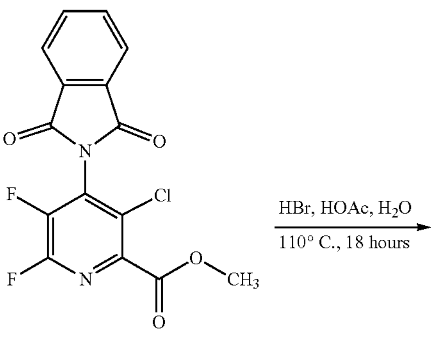

6

-continued

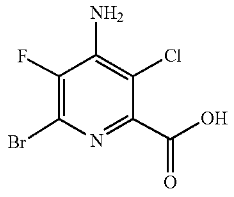

Formula A1

A mixture of compound 6 (3.92 g, 11.1 mmol), water (2 mL, 111 mmol) and anhydrous hydrogen bromide (HBr) in HOAc (5.7 M; 78 mL, 445 mmol) was heated at 110° C. for 18 hours in a 500 mL sealed flask. The reaction mixture was cooled to 0° C. and quenched with water (400 mL). The resulting suspension was stirred for 30 minutes at 0° C. and filtered, and the collected solid was washed with water (2×100 mL) and hexanes (3×100 mL). The title compound was isolated as a beige solid (2.08 g, 54%, HPLC purity 96.5%): mp 211.3-212.5° C.; 1H NMR (DMSO-$d_6$) δ 13.72 (br s, 1H), 7.16 (br s, 2H); $^{19}$F NMR (DMSO-$d_6$) δ −130.28.

Example 21: Preparation of 4-amino-6-bromo-3-chloro-5-fluoropicolinic Acid (Formula A1)

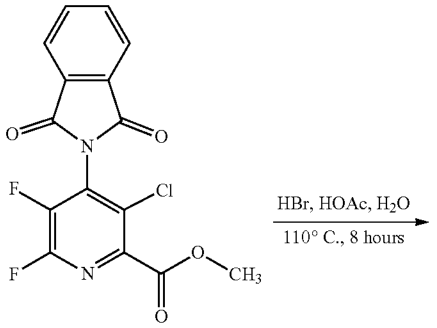

6

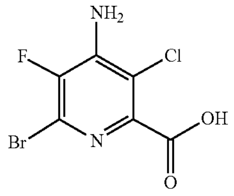

Formula A1

In a 1-L Hastelloy $C_{276}$ reactor, compound 6 (50 g, 0.142 mol) was suspended in water (8.93 g, 0.496 mol), and HBr (57.5 g, 0.71 mol) in acetic acid (117 g) was added. The reactor was heated to 110° C. with agitation and maintained at 110° C. for 8 hours. The reactor was cooled to 60° C. and filtered. The wet cake was washed with water (2×150 mL) and dried. The title compound was isolated as an off-white solid (42.6 g, 90%, 90% purity).

Example 22: Preparation of 4-amino-6-bromo-3-chloro-5-fluoropicolinic acid (Formula A1)

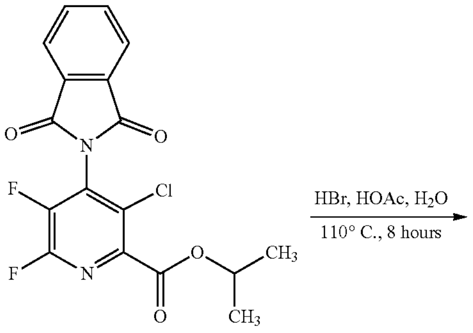

7

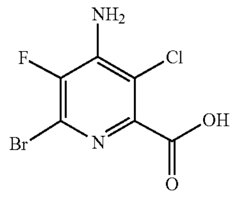

Formula A1

In a 1-L Hastelloy $C_{276}$ reactor, compound 7 (50 g, 0.13 mol) was suspended in water (8.25 g, 0.46 mol), and HBr (53.0 g, 0.65 mol) in acetic acid (108 g) was added. The reactor was heated to 110° C. with agitation and maintained at 110° C. for 8 hours. The reactor was cooled to 60° C. and filtered. The wet cake was washed with water (2×150 mL) and dried. The title compound was isolated as an off-white solid (39.3 g, 90%, HPLC purity 90%).

Example 23: Preparation of 4-amino-6-bromo-3-chloro-5-fluoropicolinic Acid (Formula A1)

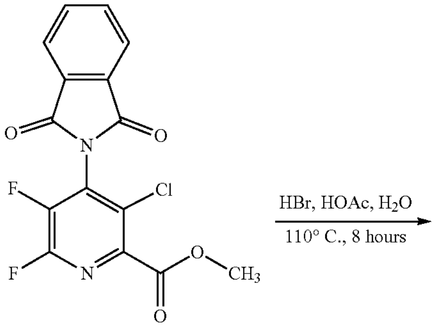

6

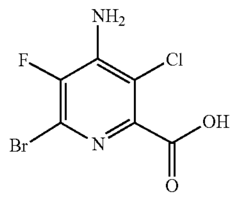

Formula A1

In a 1-L Hastelloy $C_{276}$ reactor, compound 6 (50 g, 0.142 mol) was suspended in a mixture of water (8.93 g, 0.496 mol) and a solution of HBr (57.5 g, 0.71 mol) in acetic acid (117 g). The reactor was heated to 110° C. with agitation, maintained at temperature for 8 hours, cooled to 60° C., and filtered. The filtered wet cake was reslurried in 50 weight percent (wt %) aqueous methanol (150 g) at 60° C. for 1 hour and filtered. The wet cake was dried to provide the title compound as an off-white solid (33.7 g, 88%, HPLC purity 99.1%).

Example 24: Preparation of 4-amino-6-bromo-3-chloro-5-fluoropicolinic acid (Formula A1)

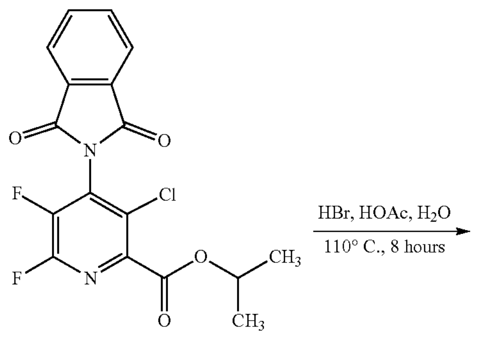

7

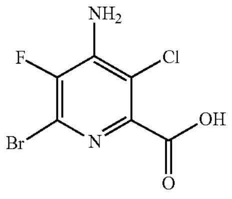

Formula A1

In a 1-L Hastelloy $C_{276}$ reactor, compound 7 (50 g, 0.13 mol) was suspended in a mixture of water (8.25 g, 0.46 mol) and a solution of HBr (53.0 g, 0.65 mol) in acetic acid (108 g). The reactor was heated to 110° C. with agitation, maintained at temperature for 8 hours, cooled to 60° C., and filtered. The filtered wet cake was reslurried in 50 wt % aqueous methanol (150 g) at 60° C. for 1 hour and filtered. The wet cake was dried to provide the title compound as an off-white solid (31.4 g, 88%, HPLC purity 99.0%).

Example 25: Preparation of 4-amino-6-bromo-3-chloro-5-fluoropicolinic Acid (Formula A1)

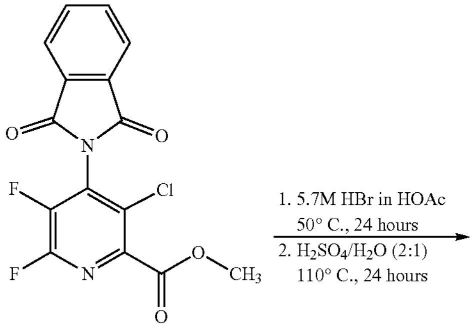

6

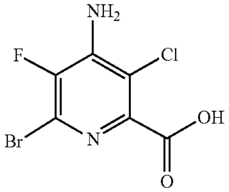

Formula A1

Step 1: A Chemglass high pressure vessel (75 mL) equipped with magnetic stirrer was charged with compound 6 (5.0 g, 14.2 mmol) and HBr in HOAc (5.7 M; 25 mL, 142 mmol). The flask was sealed with a PTFE cap and heated at 50° C. for 24 hours. The reaction mixture was cooled to 0° C. and quenched with water (50 mL). The suspension was stirred for 30 minutes at room temperature and filtered. The solid was washed with water (2×30 mL) and dried.

Step 2: To the resultant mixture from Step 1 was added a mixture of sulfuric acid and water ($H_2SO_4/H_2O$, 2:1 (v/v); 40 mL). The mixture was stirred at 110° C. for 24 hours, cooled to 0° C., and quenched with water (200 mL). The suspension was stirred for 30 minutes at room temperature and filtered. The solid was suspended in water (200 mL), and the mixture was heated at 110° C. for 1 hour. The hot suspension was filtered and dried to obtain the title compound (2.67 g, 70% over 2 steps, HPLC purity 90.3%).

Example 26: Preparation of 4-amino-3,6-dichloro-5-fluoropicolinic Acid (12)

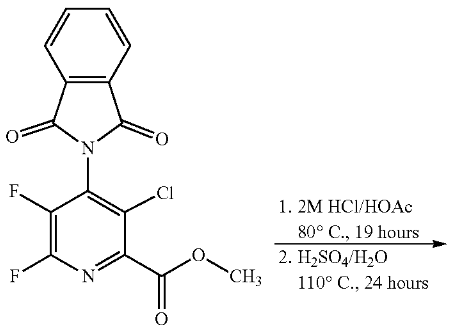

6

-continued

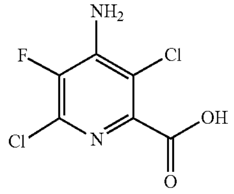

12

Step 1: Compound 6 (2.5 g, 7.1 mmol) was suspended in HCl in HOAc (2 M; 17.5 mL, 35 mmol) in a 75 mL glass sealed flask. The mixture was stirred at 80° C. (oil bath) for 19 hours. The reaction mixture was cooled to 5° C. and poured into ice-water (60 mL). The mixture was stirred for 30 minutes and filtered. The white solid (4.5 g, wet) was used in the next reaction without further purification.

Step 2: To the mixture from Step 1 was added a mixture of $H_2SO_4/H_2O$ (2:1 v/v; 20 mL). The mixture was stirred at 110° C. for 24 hours, cooled to 0° C., and quenched with water (100 mL). The suspension was stirred for 30 minutes at room temperature and filtered. The solid was suspended in 100 mL of water, and the mixture was heated at 110° C. for 1 hour. The hot suspension was filtered and dried to obtain the title compound (1.10 g, 60% over 2 steps, HPLC purity 91.4%).

Example 27: Preparation of Cyanomethyl 4-amino-6-bromo-3-chloro-5-fluoropicolinate (Formula A2)

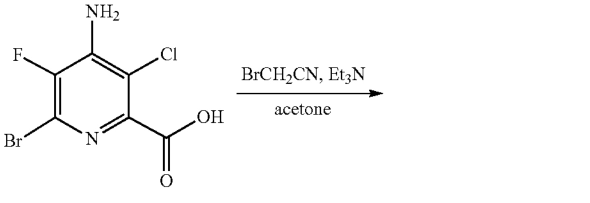

Formula A1

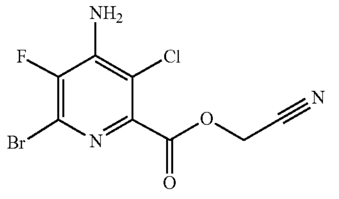

Formula A2

A 125 mL round bottom flask equipped with a magnetic stir bar was charged with 4-amino-6-bromo-3-bromo-5-fluoropicolinic acid (Formula A1; 2.0 g, 7.42 mmol) and acetone (30 mL). Bromoacetonitrile (1.03 mL, 14.8 mmol) was added. Triethylamine (4.14 mL, 29.7 mmol) was added dropwise. A white precipitate formed, and additional acetone (10 mL) was added. After 25.5 hours, additional triethylamine (1.04 mL, 7.42 mmol), bromoacetonitrile (0.517 mL, 7.42 mmol) and acetone (10 mL) were added. The reaction mixture was stirred for an additional 22.5 hours, and the volatiles were removed under reduced pressure. The resulting material was suspended in ethyl acetate and washed with water. The layers were separated, and the organic layer was dried over sodium sulfate ($Na_2SO_4$), filtered, and concentrated under reduced pressure to provide the title compound as an off-white solid (1.37 g, 60%): $^1$H NMR (600 MHz, DMSO-$d_6$) δ 7.34 (s, 2H), 5.27 (s, 2H); $^{19}$F NMR (564 MHz, DMSO-$d_6$): δ −127.73.

Example 28: Preparation of Cyanomethyl 4-amino-6-bromo-3-chloro-5-fluoropicolinate (Formula A2)

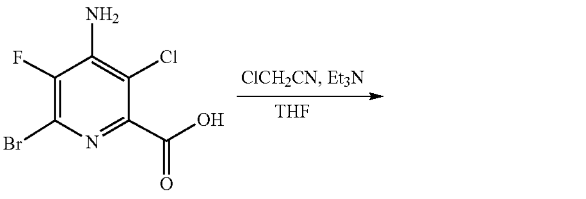

Formula A1

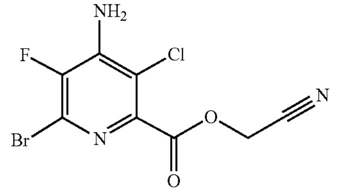

Formula A2

To a solution of 4-amino-6-bromo-3-chloro-5-fluoropicolinic acid (Formula A1; 0.5 g, 1.86 mmol) in dry THF (6.19 mL) were added sequentially 2-chloroacetonitrile (0.235 mL, 3.71 mmol) and triethylamine (1.29 mL, 7.42 mmol) dropwise. The reaction mixture was stirred for 16 hours. The reaction mixture was concentrated, and the residue was taken up in EtOAc and washed with 10% citric acid. The organic layer was washed with brine, dried over magnesium sulfate, filtered and concentrated to afford a pale pink solid. The solid was washed with 10:1 hexanes-methyl tert-butyl ether (MTBE) to afford the title compound as an off-white solid (0.57 g, 51% yield): $^1$H NMR (500 MHz, DMSO-$d_6$) δ 7.34 (s, 2H), 5.27 (s, 2H); $^{19}$F NMR (471 MHz, DMSO-$d_6$) δ −127.74.

Example 29: Preparation of 7-fluoro-1-(trimethylsilyl)-1H-indole (13)

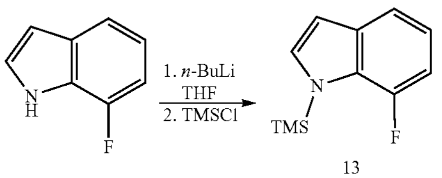 [SMILES: Fc1cccc2cc[nH]c12 ; C[Si](C)(C)n1ccc2cccc(F)c21]

13

A solution of 7-fluoro-1H-indole (5.00 g, 36.3 mmol) in anhydrous THF (80 mL) was prepared under nitrogen in a 250 mL three-neck flask equipped with addition funnel, thermocouple, magnetic stir bar, and nitrogen inlet. The flask was cooled to −78° C. n-Butyllithium (n-BuLi, 2.5 M in hexanes; 16 mL, 39.9 mmol) was added dropwise over 15 min at a rate which kept the reaction temperature below −60° C. After 1 hour, a solution of chlorotrimethylsilane (6.5 mL, 50.2 mmol) in THF (10 mL) was added dropwise. After 75 minutes, the reaction mixture was allowed to warm to ambient temperature. The reaction mixture was concentrated under vacuum. The resulting oil was slurried in dichloromethane and filtered to remove solids. The filtrate was concentrated by rotary evaporation. The title compound was isolated as a yellow oil (7.4 g, 95%): 1H NMR (400 MHz, $CDCl_3$) δ 7.28 (d, J=7.8 Hz, 1H), 7.07 (d, J=3.1 Hz, 1H), 6.91 (td, J=7.8, 4.5 Hz, 1H), 6.77 (dd, J=12.6, 7.8 Hz, 1H), 6.48 (t, J=3.2 Hz, 1H), 0.41 (d, J=2.4 Hz, 9H); $^{19}F$ NMR (376 MHz, $CDCl_3$) δ −125.16; $^{13}C\{^1H\}$ NMR (101 MHz, $CDCl_3$) δ 150.21 (d, $J_{C-F}$=243.4 Hz), 135.16 (d, $J_{C-F}$=6.1 Hz), 130.81, 127.47 (d, $J_{C-F}$=11.7 Hz), 119.91 (d, $J_{C-F}$=6.9 Hz), 115.98 (d, $J_{C-F}$=3.2 Hz), 106.50 (d, $J_{C-F}$=19.0 Hz), 104.38 (d, $J_{C-F}$=2.1 Hz), 0.03 (d, $J_{C-F}$=6.0 Hz).

Example 30: Preparation of 7-fluoro-1-(trimethylsilyl)-1H-indole (13)

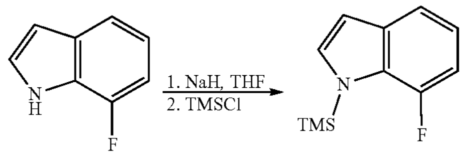

13

Sodium hydride (60% dispersion in mineral oil; 3.2 g, 57.5 mmol) was suspended in anhydrous THF (275 mL) under nitrogen in a 1000 mL 3-neck flask equipped with thermocouple, reflux condenser, magnetic stir bar, and nitrogen inlet. The mixture was stirred at 55° C. for 10 minutes. A solution of 7-fluoro-1H-indole (10.0 g, 72.5 mmol) in anhydrous THF (30 mL) was added via syringe. After 30 minutes, neat chlorotrimethylsilane (12.8 mL) was added via syringe. After 4 hours, the reaction mixture was cooled to 40° C., and additional sodium hydride (1.50 g) and chlorotrimethylsilane (5.22 g) were added. After heating at 55° C. for an additional 1 hour, the reaction mixture was concentrated by rotary evaporation. The residue was dissolved in dichloromethane and filtered. The filtrate was concentrated by rotary evaporation to a yellow oil which was purified by Kugelrohr distillation (80-85° C., 3.8 torr).

The title compound was isolated as a yellow liquid (11.1 g, 72%).

Example 31: Preparation of 1-(tert-butyldimethylsilyl)-7-fluoro-1H-indole (14)

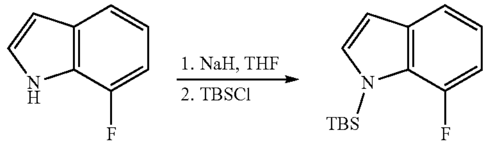

14

7-Fluoro-1H-indole (96.0 g, 701 mmol) and tert-butyldimethylsilyl chloride (TBSCl; 127.4 g, 841.2 mmol) were added to a 2-L round bottom flask under nitrogen. Anhydrous THF (580.9 g, 653.4 mL) was added to the flask, and the mixture was stirred. To a dry 2-L three-neck round bottom flask under nitrogen were added NaH (60% dispersion in mineral oil; 35.0 g, 876 mmol) and anhydrous THF (141.5 g) to create a suspension. The flask containing the NaH was cooled to 0° C. in an ice bath. An addition funnel was fitted to the flask, and the TBSCl/7-fluoroindole solution was added to the funnel. The TBSCl/7-fluoroindole solution was added to the NaH slurry over approximately 30 minutes keeping the reaction temperature at 20° C. while venting the hydrogen gas generated. After the addition was complete, the reaction flask was removed from the ice bath and the reaction mixture was stirred for one hour. Stirring was stopped and the reaction mixture was allowed to settle. The clear red supernatant solution was removed from the vessel and filtered in-line using a Whatman Polycap HD 36 filter with 10 micron (μm) pore size. After the filtration was complete, the remaining NaH in the filter was quenched with isopropyl alcohol and water. A solution of the title compound (770.0 g 20.56 wt %, 91%) was obtained. The remaining 9% mass balance was found to be 1-(tert-butyldimethylsilyl)-7-fluoro-1H-indole retained on the residual solids from the reaction.

Example 32: Preparation of 1-(tert-butyldimethylsilyl)-7-fluoro-1H-indole (14)

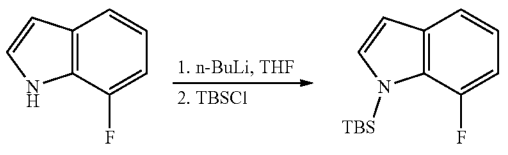

14

A solution of 7-fluoro-1H-indole (10.0 g, 74 mmol) in anhydrous THF (100 mL) was prepared under nitrogen in a 250 mL three-neck flask equipped with a thermocouple, magnetic stir bar, and nitrogen inlet. The reaction mixture was cooled to 0° C. n-BuLi (2.5 M in hexanes; 81 mmol) was added via a peristaltic pump at a rate which kept the reaction temperature below 10° C. After 30 minutes, a solution of $TBSC_1$ (13.4 g, 89 mmol) in THF (30 mL) was added.

After 90 minutes, the reaction mixture was allowed to warm to ambient temperature. The reaction mixture was carried on to the next step without further manipulation.

Example 33: Preparation of 1-(tert-butyldimethylsilyl)-7-fluoro-1H-indole (14)

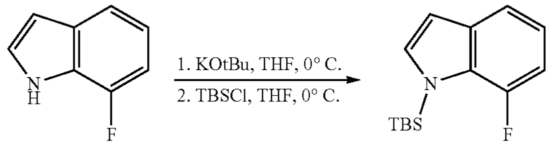

14

A 3-L reactor equipped with a nitrogen gas inlet, temperature probe, and overhead stirrer was charged with potassium tert-butoxide (183 g, 1.595 mol) and THF (900 mL). The solution was cooled to 0° C. After the temperature stabilized at 0° C., A solution of 7-fluoro-1H-indole (200 g, 1.450 mol) in THF (600 mL) was added to the reaction via a peristaltic pump (10 mL per minute), and the reaction mixture was allowed to stir for 30 minutes after the addition was complete. A solution of $TBSC_1$ (262 g, 1.740 mol) in THF (600 mL) was added via pump (10 mL per minute), and the reaction mixture was allowed to stir for 0.6 hours at 0° C. After 0.6 hours, heptanes (1.8 L) was added to the reactor. The reaction mixture was quenched at 0° C. with saturated ammonium chloride (300 mL) and water (1.2 L). The reaction mixture was stirred for 5 minutes after which the stirring was paused and the layers were separated. The aqueous layer was drained and additional water (1.2 L) was added. The reaction mixture was stirred for 5 minutes after which the stirring was paused and the layers were separated. The aqueous layer was drained. The organic layer was drained, concentrated under reduced pressure, and co-evaporated by azeotrope with acetonitrile (3×100 mL). The title compound was isolated as an orange oil (351 g, 97%). Karl Fischer titration analysis showed less than 0.1% water in the product. 1H NMR (500 MHz, $CDCl_3$) δ 7.39 (d, J=7.8 Hz, 1H), 7.24 (d, J=3.2 Hz, 1H), 7.03 (td, J=7.8, 4.4 Hz, 1H), 6.87 (dd, J=13.0, 7.8 Hz, 1H), 6.63 (t, J=3.1 Hz, 1H), 0.92 (s, 9H), 0.58 (s, 3H), 0.57 (s, 3H); 13C NMR (126 MHz, $CDCl_3$) δ 150.4 (d, J=245 Hz), 135.7 (d, J=6.3 Hz), 132.8, 128.5 (d, J=11.4 Hz), 120.5 (d, J=7.6 Hz), 116.5 (d, J=2.5 Hz), 107.5 (d, J=20.2 Hz), 105.3 (d, J=1.3 Hz), 26.46, 19.55, −2.86, −2.94; 19F NMR (471 MHz, $CDCl_3$) δ −121.56.

Example 34: Preparation of 7-fluoro-6-(4,4,5,5-tetramethyl-1,3,2-dioxaborolan-2-yl)-1H-indole (Formula B1-1)

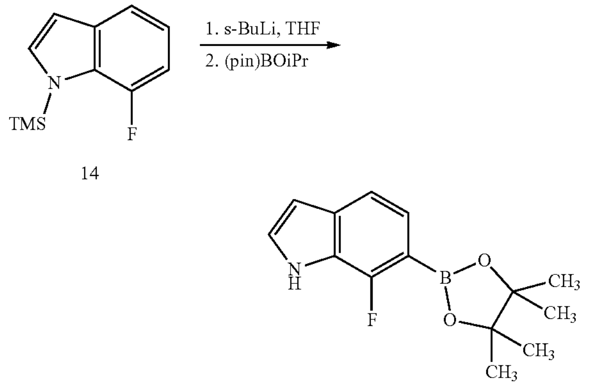

14

Formula B1-1

A solution of 7-fluoro-1-(trimethylsilyl)-1H-indole (13; 400 mg, 1.77 mmol) in anhydrous THF (10 mL) was prepared under nitrogen. The solution was cooled to −78° C. sec-Butyllithium (s-BuLi, 1.4 M in cyclohexanes; 125 mg, 1.95 mmol) was added dropwise. After 2 hour at −78° C., neat 2-isopropoxy-4,4,5,5-tetramethyl-1,3,2-dioxaborolane (330 mg, 1.77 mmol) was added via syringe. After an additional hour, the reaction mixture was quenched with methanol, concentrated, and dissolved in a small amount of DMSO. Purification by reverse phase chromatography ($C_{18}$ column, 0.1% formic acid ($HCO_2H$, aq)-acetonitrile gradient) gave the title compound (128 mg, 28%). NMR spectral data and HPLC retention time matched those of an authentic sample. 1H NMR (500 MHz, $CDCl_3$) δ 8.53 (s, 1H), 7.44-7.35 (m, 2H), 7.27-7.21 (m, 1H), 6.56 (td, J=3.3, 2.3 Hz, 2H), 1.38 (s, 13H); $^{19}F$ {$^{1}H$} NMR (471 MHz, $CDCl_3$) δ −124.34; $^{11}B$ NMR (160 MHz, $CDCl_3$) δ 30.83.

Example 35: Preparation of (7-fluoro-1H-indol-6-yl)boronic Acid (Formula B1-2)

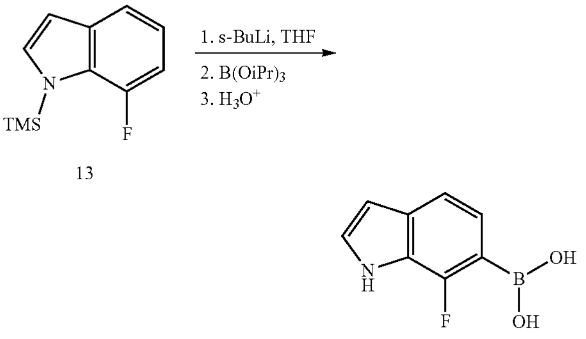

13

Formula B1-2

A 1 L three-neck round bottom flask equipped with addition funnel, nitrogen inlet, thermocouple, and mechanical stirrer was charged with 7-fluoro-1-(trimethylsilyl)-1H-indole (13; 20 g, 96 mmol) in anhydrous THF (191 ml). The solution was cooled in a dry ice-acetone bath to −77° C. s-BuLi (1.4 M in cyclohexanes; 76 mL, 96 mmol) was transferred by cannula under nitrogen into the addition funnel and added dropwise over 25 minutes. The addition rate was controlled to keep the temperature below −70° C. After 1 hour, additional s-BuLi solution (30 mL) was added over 10 minutes. After an additional 1 hour, triisopropyl borate (24.2 mL, 105 mmol) was transferred to the addition funnel and added dropwise, keeping the temperature below −70° C. After 90 minutes, the cooling bath was removed, and reaction was warmed 0° C. The reaction was quenched by slow addition of water (500 mL). EtOAc was added, and the organic layer was separated. The aqueous layer was cooled in an ice-water bath while glacial acetic acid was added dropwise until the mixture was pH 5. EtOAc was added to the acidic aqueous layer, and the organic layer was separated. The organic layer was dried over sodium sulfate and concentrated. The resulting solid was suspended in hexanes, filtered, washed with hexanes, and dried. The title compound was isolated as a white crystalline solid (10.4 g, 61%): $^{1}H$ NMR (300 MHz, DMSO-$d_6$) δ 11.53 (s, 1H, NH), 7.94 (s, 2H, BOH), 7.39 (t, J=2.8 Hz, 1H), 7.30 (dt, J=7.9, 0.9 Hz, 1H), 7.16 (dd, J=7.9, 5.2 Hz, 1H), 6.48 (ddd, J=3.6, 3.0, 1.9 Hz, 1H); $^{19}F$ {$^{1}H$} NMR (471 MHz, DMSO-$d_6$) δ −124.25; ESIMS m/z 177.9 ([M−H]$^-$).

Example 36: Preparation of (1-(tert-butyldimethylsilyl)-7-fluoro-1H-indol-6-yl)boronic acid (Formula B1-3)

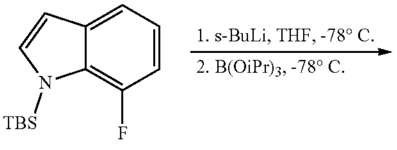

14

-continued

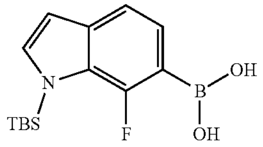

Formula B1-3

A 100 mL three-neck round bottom flask equipped with a nitrogen gas inlet, temperature probe, and overhead stirrer was charged with 1-(tert-butyldimethylsilyl)-7-fluoro-1H-indole (14; 4.74 g, 19 mmol). Anhydrous THF (40 mL) was added, and the solution was stirred at 200 RPM under nitrogen for 20 minutes at room temperature. The reaction was cooled to −70 to −78° C. (dry ice-acetone bath). s-BuLi (1.4 M in cyclohexane; 16.9 mL, 22.8 mmol) was added via syringe while maintiaing an internal temperature of or below −70° C. After the addition was complete, the reaction mixture was stirred at −70 to −78° C. for 2 hours. Triisopropylborate (5.29 mL, 22.8 mmol) was added slowly while maintaining a temperature of or below −70° C. The reaction mixture was allowed to stir at −70 to −78° C. for 45 minutes. A light yellow/white slurry formed. The dry ice-acetone bath was removed, and while still cold (−30° C.), water (10 mL) and saturated ammonium chloride solution (10 mL) were added sequentially. The reaction mixture was further diluted with EtOAc (~250 mL) and water (50 mL). The aqueous layer was extracted EtOAc (250 ml). The pH of the aqueous layer was ~10. Additional saturated ammonium chloride solution was added, and the mixture was extracted with EtOAc (250 mL). The pH of the aqueous layer was ~9-10. The organic extracts were dried over sodium sulfate and concentrated to dryness. A light yellow oil was obtained and transfered to a 40 mL vial. To the oil was added a layer of hexanes and the vial placed in the freezer overnight. A white precipitate formed and when stirred, the lower level of yellow oil also solidified. Additional hexanes (~10 mL) was added to the vial, and the liquid was decanted. The title compound was isolated as an off-white powder after drying under vacuum (4.9 g, 88% yield): $^{1}$H NMR (400 MHz, DMSO-$d_6$) δ 7.46-7.24 (m, 2H), 7.02 (dd, J=7.8, 4.4 Hz, 1H), 6.62 (t, J=3.3 Hz, 1H), 0.90 (s, 9H), 0.59 (d, J=3.2 Hz, 6H); $^{19}$F NMR (376 MHz, DMSO) δ −114.88, −147.16, −152.54, −181.34.

Example 37: Preparation of Lithium (1-(tert-butyldimethylsilyl)-7-fluoro-1H-indol-6-yl)triisopropoxyborate (Formula B2-1)

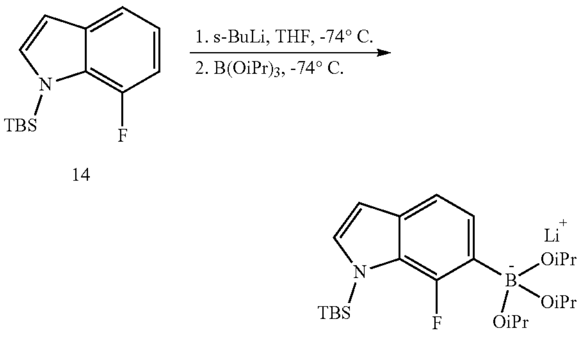

14

Formula B2-1

A 1-L three-neck round bottom flask equipped with a nitrogen gas inlet, temperature probe, and overhead stirring was charged with 1-(tert-butyldimethylsilyl)-7-fluoro-1H-indole (14; 36.4 g, 146 mmol). Anhydrous THF (239 mL) was added, and the solution was stirred at 200 RPM under nitrogen for 20 minutes at room temperature. The reaction mixture was cooled to −70 to −78° C. (dry ice-acetone bath). s-BuLi (1.4 M in cyclohexane; 125 mL, 175 mmol) was added dropwise via a peristaltic pump while maintaining an internal temperature of or below −70° C. over a period of 0.5 to 1 hour. After the addition of s-BuLi was complete, the reaction mixture was stirred at −70 to −78° C. for 2 hours. Triisopropylborate (40.6 mL, 175 mmol) was added dropwise while maintaining a temperature of or below −70° C. over 20 to 30 minutes. The reaction mixture was allowed to stir at −70 to −78° C. for 45 minutes. Over time, the reaction mixture turned from yellow to a light yellow/white slurry. Following the reaction period, the reaction was quenched with 2-propanol (5.62 mL, 72.9 mmol) at −74° C.

The reaction mixture was warmed to room temperature, at which time the milky solution turned to a homogenous yellow solution. The contents were transferred to a 2-L four-neck round bottom flask equipped with overhead stirring and a connection to a vacuum pump. The vacuum distillation took place at room temperature with overhead stirring (200 RPM). The solution was distilled until a slurry was obtained after which additional anhydrous acetonitrile (200 mL) was added via the funnel, and the second distillation took place to yield a slurry. A second portion of anhydrous acetonitrile (200 mL) was added via the funnel, and the second distillation took place yield a green-brown slurry. At this time, the reaction was sampled by removing a small aliquot dissolved in methanol-$d_4$ (0.5 mL). The aliquot was analyzed by 11-1 and $^{19}$F NMR spectroscopy. Analysis by $^{19}$F NMR spectroscopy indicated ~94% conversion to the desired borate. The title compound was used on the same day or stored overnight in the refrigerator under nitrogen.

Alternatively, the title compound can be isolated as a solid. Using the procedure above with 1-(tert-butyldimethylsilyl)-7-fluoro-1H-indole (14; 15 g, 60.1 mmol), the reaction mixture was warmed to room temperature, the volatiles were removed, and hexanes were added. A white solid precipitated, was filtered and was washed with heptanes. The white filter cake was dried under vacuum to obtain a white solid (25.5 g, 96%): $^{1}$H NMR (400 MHz, methanol-$d_4$) δ 7.20 (dd, J=7.8, 4.7 Hz, 1H), 7.14-7.06 (m, 2H), 6.41 (t, J=3.2 Hz, 1H), 3.87 (hept, J=6.1 Hz, 3H), 1.10 (d, J=6.2 Hz, 18H), 0.85 (d, J=1.1 Hz, 9H), 0.52 (d, J=3.3 Hz, 6H); $^{19}$F NMR (376 MHz, methanol-$d_4$) δ −116.19.

Example 38: Preparation of Lithium (1-(tert-butyldimethylsilyl)-7-fluoro-1H-indol-6-yl) trimethoxyborate (Formula B2-2)

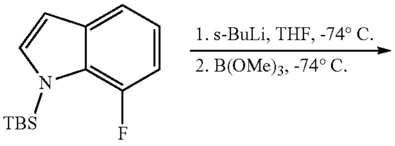

14

-continued

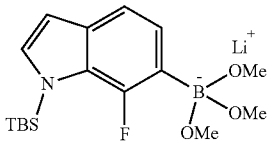

Formula B2-2

A 0.5-L three-neck round bottom flask equipped with a nitrogen gas inlet, temperature probe, and overhead stirring was charged with 1-(tert-butyldimethylsilyl)-7-fluoro-1H-indole (14; 10 g, 40.1 mmol). Anhydrous THF (66 mL) was added, and the solution was stirred at 200 RPM. The reaction mixture was cooled to −70 to −78° C. (dry ice-acetone bath). s-BuLi (1.4 M in cyclohexane; 34.4 mL, 48.1 mmol) was added dropwise while maintaining an internal temperature of or below −70° C. After the addition of s-BuLi was complete, the reaction mixture was stirred at −70 to −78° C. for 2 hours. Trimethylborate (5.38 mL, 48.1 mmol) was added dropwise while maintaining a temperature of or below −70° C. over 20 to 30 minutes. The reaction mixture was allowed to stir at −70 to −78° C. for 40 minutes. Following the reaction period, the reaction was quenched with methanol (0.811 mL, 20.1 mmol) at −74° C. The volatiles were removed and the title compound was used in the next step without further manipulation.

Example 39: Preparation of 4-amino-3-chloro-5-fluoro-6-(7-fluoro-1H-indol-6-yl)picolinic Acid (Formula I-A)

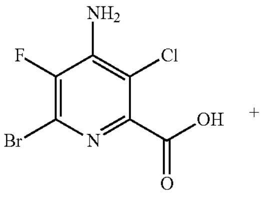

Formula A1

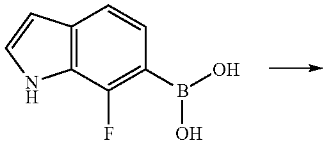

Formula B1-2

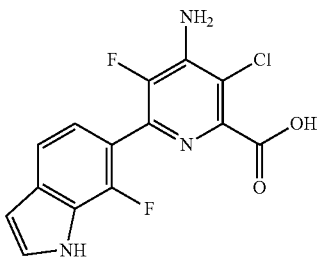

Formula I-A

To a vial in the glove box were added palladium(II) acetate ($Pd(OAc)_2$; 83 mg, 0.371 mmol), triphenylphosphine ($PPh_3$; 214 mg, 0.816 mmol) and acetonitrile (16 mL). A bright yellow slurry formed. 4-Amino-6-bromo-3-chloro-5-fluoropicolinic acid (Formula A1; 2 g, 7.42 mmol) and 7-fluoro-1H-indol-6-yl boronic acid (x; 1.86 g, 10.4 mmol) were added as solids. A degassed solution of aqueous potassium carbonate (1.85 g, 13.4 mmol, 8 mL) was added, and the resulting orange solution heated to 70° C. An aliquot was removed for analysis by $^{19}F$ NMR after 3.5 hours. The reaction mixture was cooled to room temperature and diluted with water and ethyl acetate. The layers were separated. The aqueous layer was made acidic with 1 M HCl. A beige precipitate formed, that was filtered and dried under vacuum to afford the title compound (2.0 g, 83%). The analytical data matched that in the literature.

Example 40: Preparation of 4-amino-3-chloro-5-fluoro-6-(7-fluoro-1H-indol-6-yl)picolinic Acid (Formula I-A)

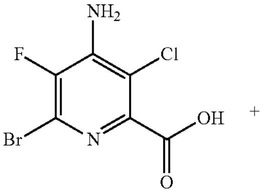

Formula A1

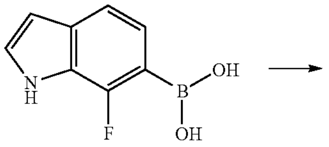

Formula B1-2

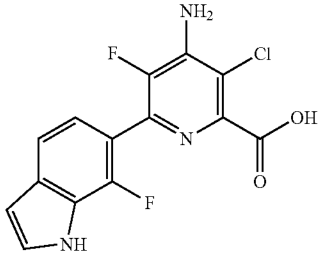

Formula I-A

To a vial in the glovebox were added dichloro[1,1'-bis(di-cyclohexylphosphino)ferrocene]palladium(II) (5 mol %), potassium carbonate (46.2 mg, 0.334 mmol), 4-amino-6-bromo-3-chloro-5-fluoropicolinic acid (Formula A1; 50 mg, 0.186 mmol), and (7-fluoro-1H-indol-6-yl)boronic acid (Formula B1-2; 39.8 mg, 0.223 mmol). THF (1.2 mL) was added. The reaction mixture was heated to 70° C. and stirred at 500 RPM for 15-16 hours.

The vial was removed from the glovebox. The reaction mixture was diluted with DMSO-$d_6$ (0.5 mL) and 4-fluorotoluene (20 μL, as an internal standard). A 10-second relaxation delay time was set on the NMR spectrometer for $^{19}F$ NMR spectral analysis. Analysis by $^{19}F$ NMR spectroscopy indicated a 55% yield.

Example 41: Preparation of 4-amino-3-chloro-5-fluoro-6-(7-fluoro-1H-indol-6-yl)picolinic Acid (Formula I-A)

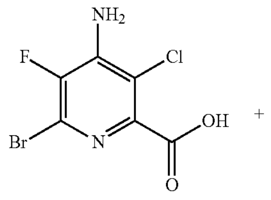

Formula A1

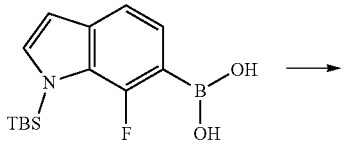

Formula B1-3

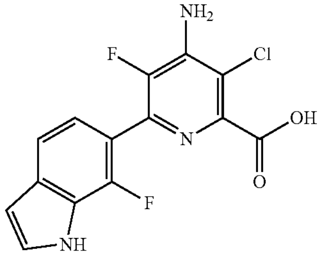

Formula I-A

To a vial in the glove box were added dichlorobis(triphenylphosphine)palladium(II) ($PdCl_2(PPh_3)_2$; 6.51 mg, 9.28 μmol), potassium carbonate (56.4 mg, 0.408 mmol), (1-(tert-butyldimethylsilyl)-7-fluoro-1H-indol-6-yl)boronic acid (Formula B1-3; 65.3 mg, 0.223 mmol), and 4-amino-6-bromo-3-chloro-5-fluoropicolinic acid (Formula A1; 50 mg, 0.186 mmol). To the solids were added acetonitrile (0.8 mL) and water (degassed, 0.4 mL). The reaction mixture was heated to 70° C. and stirred at 500 RPM for 24 hours. The vial was removed from the glovebox. The reaction mixture was diluted with DMSO-$d_6$ (0.5 mL) and 4-fluorotoluene (20 μL, as an internal standard). A second relaxation delay time was set on the NMR spectrometer for $^{19}F$ NMR analysis. Analysis by $^{19}F$ NMR spectroscopy indicated a 96% yield.

Example 42: Preparation of 4-amino-3-chloro-5-fluoro-6-(7-fluoro-1H-indol-6-yl)picolinic Acid (Formula I-A)

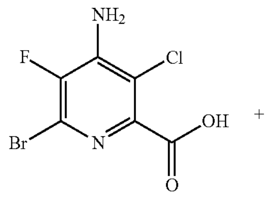

Formula A1

-continued

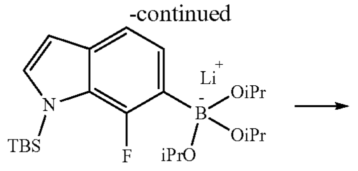

Formula B2-1

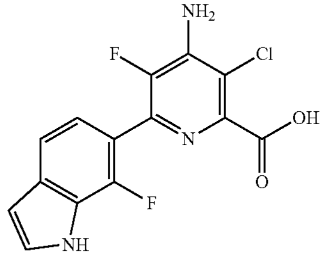

Formula I-A

To a 2-L four-neck round bottom flask equipped with a nitrogen gas inlet, temperature probe, reflux condenser, and overhead stirring (200 RPM) were added lithium (1-(tert-butyldimethylsilyl)-7-fluoro-1H-indol-6-yl)triisopropoxyborate (Formula B2-1; 60.9 g, 137 mmol) and anhydrous acetonitrile (483 mL), and the reaction mixture was purged for with nitrogen 20 minutes. A solution of sodium hydroxide (4.64 g, 116 mmol) dissolved in water (242 mL, degassed for 1 hour) was added. 4-Amino-6-bromo-3-chloro-5-fluoropicolinic acid (Formula A1; 28.4 g, 106 mmol) was added as a solid. The reaction mixture was purged for an additional 10 minutes, and $PdCl_2(PPh_3)_2$ (1.85 g, 2.64 mmol) was added. The reaction mixture was purged with nitrogen for an additional 5 minutes before the temperature ramp was initiated. The temperature ramp was from room temperature to 60° C. over 30 minutes. After 1.5 hours of heating, additional sodium hydroxide (4.64 g, 116 mmol) was added as a solid. The reaction mixture was was allowed to stir at 60° C. for an additional 1.5 hours. After 3 hours, the reaction mixture was cooled to room temperature and the volatiles were removed under reduced pressure.

The reaction mixture was diluted with additional water (0.75 L) and transferred to a 5-L jacketed reactor. To the aqueous solution was added methyl tert-butyl ether (MTBE; 0.8 L). The reaction mixture was stirred for 30 minutes, and the layers were separated. The aqueous layer was drained into a 3-L four-neck round bottom flask. The organic layer was washed with an additional water (0.25 L). The aqueous phases were combined and the organic layer was discarded. The aqueous solution was heated to an internal temperature of 40° C. (180 RPM overhead stirring). The pH of the solution was made acidic (from pH 12 to pH 3) by dropwise addtion of HCl (6 M, ~60 mL) over a period of 40 minutes. As the pH drew closer to 3, a white precipitate began to form, and the aqueous layer turned yellow. The reaction mixture was cooled to 20° C. over a period of 6 hours. The off-white or yellow solid was filtered through a disposable plastic frit and washed with deionized water (1 L). The wet cake was dried in a vacuum oven at 40-45° C. over three days. The title compound was isolated as a light yellow to beige solid (30.1 g, 88%).

Example 43: Preparation of Cyanomethyl 4-amino-3-chloro-5-fluoro-6-(7-fluoro-1H-indol-6-yl)picolinate (I-B)

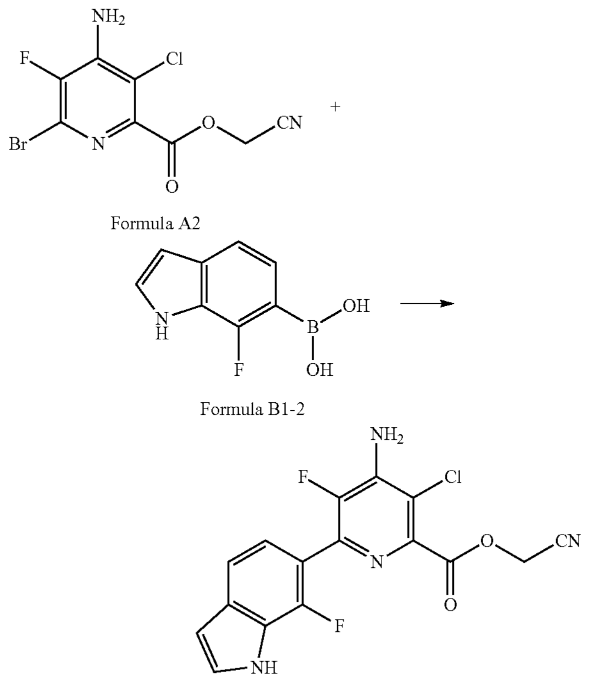

Formula A2

Formula B1-2

Formula I-B

To a 5 mL vial in the glove box were added dichloro[1,1'-bis(di-cyclohexylphosphino)ferrocene]palladium(II) (6.17 mg, 8.10 micromoles (μmol)), potassium carbonate (40.3 mg, 0.292 mmol), cyanomethyl 4-amino-6-bromo-3-chloro-5-fluoropicolinate (Formula A2; 50 mg, 0.162 mmol), and (7-fluoro-1H-indol-6-yl)boronic acid (Formula B1-2; 34.8 mg, 0.194 mmol). THF (1.2 mL) was added. The reaction mixture was heated to 70° C. and stirred at 500 RPM for 15 hours. The vial containing the reaction mixture was taken out of the glovebox, and DMSO-$d_6$ (0.5 mL) and 4-fluorotoluene (20 microliters (μL), 0.181 mmol, internal standard) were added. Analysis by $^{19}F$ NMR indicated a 40% yield Example 44: Preparation of Cyanomethyl 4-amino-3-chloro-5-fluoro-6-(7-fluoro-1H-indol-6-yl)picolinate (Formula I-B)

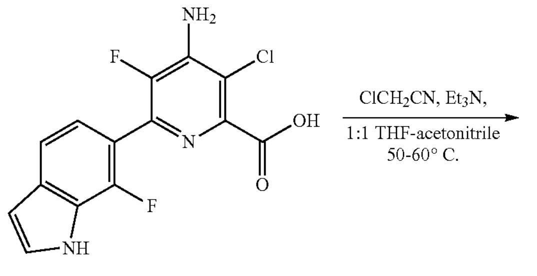

Formula I-A

-continued

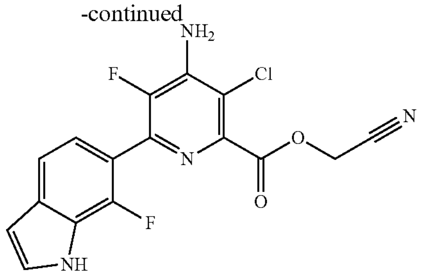

Formula I-B

In a 100 mL reactor with overhead stirring and under a nitrogen atmosphere, 4-amino-3-chloro-5-fluoro-6-(7-fluoro-1H-indol-6-yl)picolinic acid (Formula I-A; 6 g, 17.6 mmol) was taken up in acetonitrile (25 mL) and THF (25 mL). The reaction mixture was heated to 55° C. Triethylamine (2.70 mL, 19.4 mmol) was added to the solution over 2 minutes. After 15 minutes, 2-chloroacetonitrile (1.67 mL, 26.4 mmol) was added over 2 minutes. The reaction was stirred at 60° C. overnight. Analysis after 14 hour indicated >95% alkylation. The temperature was reduced to 25° C. and water (20 mL) was added to the reaction mixture, affording a homogeneous mixture. To the mixture was added EtOAc (25 mL). This afforded phase separation, and the mixture was transferred to a separatory funnel. The phases were separated, and the organic phases were washed with a mixture of water (20 mL) and sat'd brine (10 mL). The phases were separated and the organic layer collected. The solvent was evaporated to afford an oil.

The oil from the previous step (7.3 g) was taken up in isopropyl acetate (55 mL, 13.3 wt %) in a 100 mL reactor. The mixture was heated to 85° C. with stirring at 300 RPM. The mixture became a solution at this temperature. The temperature was then reduced to 70° C., and the stirring rate was reduced to 100 RPM. Nucleation was observed, and heptane was added (2 mL at 0.5 mL/min). Additional solids developed yielding a thick mixture. The stirring rate was increased to 300 RPM, and the temperature was increased to 80° C. (over 10 min). Heptane was added (17 mL at 0.5 mL/min). The mixture became very thick during addition. The stirring rate was increased to 600 RPM during addition in order to maintain mixing. Once addition was complete, the temperature was reduced to 25° C. over 30 minutes affording a thick slurry of white solids. The solids were collected by filtration. Additional heptane (~30 mL) was added to the mixture to facilitate transfer to the funnel. The solids were washed with heptane (~20 mL). The solids were dried in a vacuum oven (40° C., house vacuum) overnight. The title compound was isolated as a white solide (6.5 g, 89%): 1H NMR (300 MHz, DMSO-$d_6$) δ 11.84 (s, 1H), 7.53 (t, J=2.7 Hz, 1H), 7.48 (d, J=8.2 Hz, 1H), 7.16-7.03 (m, 3H), 6.59 (td, J=3.3, 1.8 Hz, 1H), 5.30 (s, 2H); $^{19}F$ NMR (376 MHz, DMSO-$d_6$) δ −134.20 (d, J=29.4 Hz), −136.15 (d, J=29.4 Hz).

Example 45: Preparation of cyanomethyl 4-amino-3-chloro-5-fluoro-6-(7-fluoro-1H-indol-6-yl)picolinate (Formula I-B)

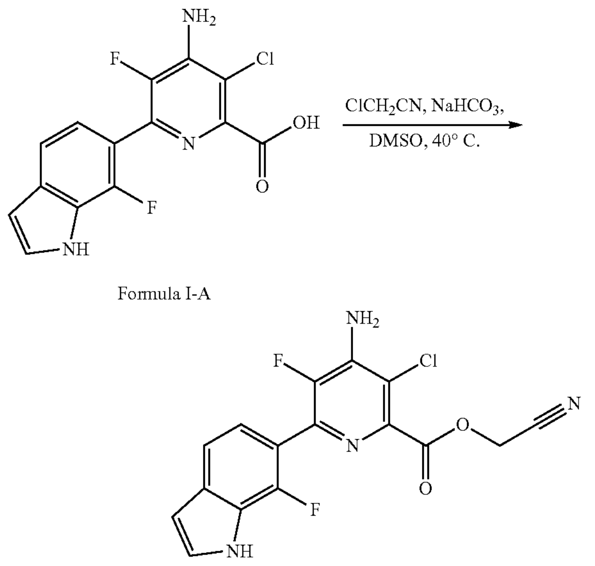

Formula I-A

Formula I-B

To a stirred solution of Formula I-A (1010 g, 3.13 mol) in DMSO (6.06 L) was added sodium bicarbonate (289 g, 3.44 mol), and the mixture was stirred for 10 minutes. 2-Chloroacetonitrile (254 mL, 4.07 mol) was added dropwise over a period of 20 minutes. The resulting reaction mixture was stirred for 3.5 hours at 40° C. The reaction mixture was cooled to room temperature, poured slowly into ice cold water (20 L), and stirred for 1 hour. The solid was filtered and dissolved in EtOAc (20 L). The solution was washed with water (30 L) and brine (10 L), dried over anhydrous sodium sulfate, and concentrated under vacuum. The title compound was isolated (953 g, HPLC purity 90%).

The compositions and methods of the claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the claims. Further, while only certain representative composition materials and method steps disclosed herein are specifically described, other combinations of the composition materials and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed.

What is claimed is:

1. A process for the preparation of a 4-amino-6-(heterocyclic) picolinate of Formula I:

Formula I

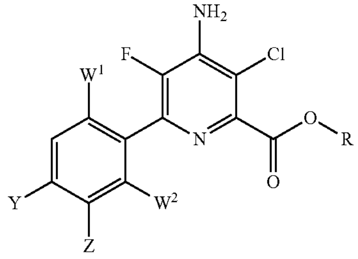

wherein

R represents H, $C_1$-$C_{12}$ alkyl, $C_3$-$C_{12}$ alkynyl, $C_1$-$C_3$ alkyl substituted with CN, or $C_6$-$C_{12}$ arylalkyl;

$W^1$ represents H or F;

$W^2$ represents H, F, $C_1$, $C_1$-$C_3$ alkyl, $C_1$-$C_3$ alkoxy, $C_1$-$C_3$ haloalkyl, or $C_1$-$C_3$ haloalkoxy;

Y represents H, halogen, $C_1$-$C_4$ alkyl, $C_1$-$C_4$ haloalkyl, $C_1$-$C_3$ alkoxy, $C_1$-$C_3$ haloalkoxy; and Z represents $C_1$-$C_4$ alkyl, $C_1$-$C_3$ alkoxy, $C_1$-$C_4$ haloalkyl, $C_1$-$C_3$ haloalkoxy, $C_1$-$C_3$ alkoxy-substituted $C_1$-$C_3$ alkyl, or —$NR^1R^2$, wherein $R^1$ and $R^2$ are independently hydrogen, $C_1$-$C_3$ alkyl, or $C_1$-$C_3$ haloalkyl; and Y and Z taken together are a 5-membered aromatic or non-aromatic, heterocyclic ring;

the process comprising the following steps:

a. creating a first mixture containing a compound of Formula A,

Formula A

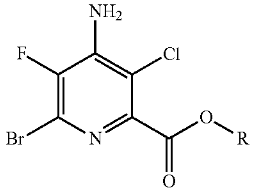

wherein

R represents H, $C_1$-$C_{12}$ alkyl, $C_3$-$C_{12}$ alkynyl, $C_1$-$C_3$ alkyl substituted with CN, or $C_6$-$C_{12}$ arylalkyl;

a compound of Formula B1 or Formula B2, or mixtures thereof,

Formula B1

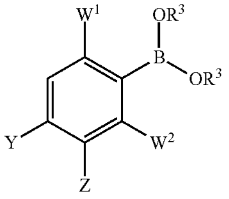

-continued

Formula B2

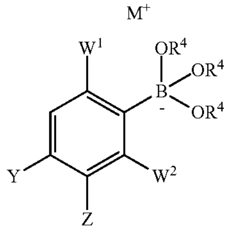

wherein $M^+$ represents an alkali metal cation;

$R^3$ represents H or $C_1$-$C_6$ alkyl, or alternatively two $R^3$ may form a $C_2$-$C_6$ alkyl linkage, which together with B and two O form a 5- to 9-atom cyclic structure;

$R^4$ represents $C_1$-$C_6$ alkyl;

$W^1$ represents H or F;

$W^2$ represents H, F, $C_1$, $C_1$-$C_4$ alkyl, $C_1$-$C_3$ haloalkyl, $C_1$-$C_3$ alkoxy or $C_1$-$C_3$ haloalkoxy;

Y represents halogen, $C_1$-$C_4$ alkyl, $C_1$-$C_4$ haloalkyl, $C_1$-$C_3$ alkoxy, $C_1$-$C_3$ haloalkoxy; and Z represents $C_1$-$C_4$ alkyl, $C_1$-$C_3$ alkoxy, $C_1$-$C_4$ haloalkyl, $C_1$-$C_3$ haloalkoxy, $C_1$-$C_3$ alkoxy-substituted $C_1$-$C_3$ alkyl, or —$NR^1R^2$, wherein $R^1$ and $R^2$ are independently hydrogen, $C_1$-$C_3$ alkyl, or $C_1$-$C_3$ haloalkyl; and Y and Z taken together are a 5-membered aromatic or non-aromatic, heterocyclic ring;

one or more bases; and one or more solvents;

b. adding a palladium catalyst, and optionally a ligand to the first mixture to form a second mixture; and c. heating the second mixture to a temperature of between about 25° C. and about 100° C.

2. The process of claim 1, wherein the 4-amino-6-(heterocyclic) picolinate of Formula I is isolated from the second mixture.

3. The process of claim 2, further comprising the steps of:

a. creating a mixture containing the 4-amino-6-(heterocyclic) picolinate of Formula I, wherein R represents H, and one of i. an acid, an alcohol ROH, and a solvent; or ii. an alkyl, alkynyl, or arylalkyl halide $RX^1$, a base, and a solvent wherein R represents $C_1$-$C_{12}$ alkyl, $C_3$-$C_{12}$ alkynyl, $C_1$-$C_3$ alkyl substituted with CN, or $C_6$-$C_{12}$ arylalkyl; and $X^1$ represents Cl, Br, or I; and b. heating the mixture at a temperature from about 25° C. to about 80° C.

4. The process of claim 3, wherein the 4-amino-6-(heterocyclic) picolinate of Formula I, wherein R represents $C_1$-$C_{12}$ alkyl, $C_3$-$C_{12}$ alkynyl, $C_1$-$C_3$ alkyl substituted with CN, or $C_6$-$C_{12}$ arylalkyl, is isolated from the mixture.

5. The process of claim 1, wherein the compound of Formula A is prepared by a second process, the process comprising the steps of:

a. creating a first mixture containing a compound of Formula $C_2$

Formula C2

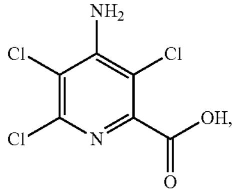

an acid or an acid chloride-forming compound, and an alcohol ROH, wherein R represents $C_1$-$C_{12}$ alkyl, $C_3$-$C_{12}$ alkynyl, $C_1$-$C_3$ alkyl substituted with CN, or $C_6$-$C_{12}$ arylalkyl;

b. heating the first mixture at a temperature from about 70° C. to about 90° C.;

c. isolating from the first mixture the compound of Formula D2

Formula D2

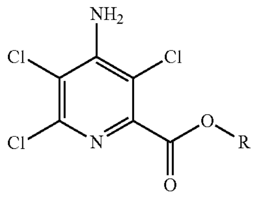

wherein

R represents $C_1$-$C_{12}$ alkyl, $C_3$-$C_{12}$ alkynyl, $C_1$-$C_3$ alkyl substituted with CN, or $C_6$-$C_{12}$ arylalkyl;

d. creating a second mixture containing the compound of Formula D2;

a phthaloyl halide or a phthalic anhydride;

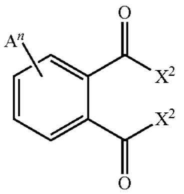

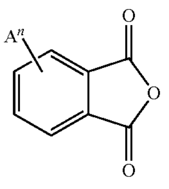

wherein

A is independently selected from H, F, Cl, Br, I, $C_1$-$C_4$ alkyl, $C_1$-$C_4$ alkoxy, $C_1$-$C_4$ haloalkyl, $C_1$-$C_4$ haloalkoxy, and nitro;

n is 1, 2, 3, or 4; and $X^2$ is Cl or Br;

a base; a solvent or solvent mixture; and optionally an acylation catalyst;

e. heating the second mixture at a temperature from about 25° C. to about 100° C.;

f. isolating from the second mixture the compound of Formula E2

Formula E2

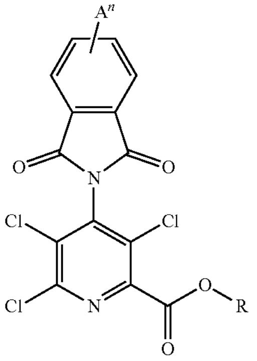

wherein

R represents $C_1$-$C_{12}$ alkyl, $C_3$-$C_{12}$ alkynyl, $C_1$-$C_3$ alkyl substituted with CN, or $C_6$-$C_{12}$ arylalkyl;

A is independently selected from H, F, Cl, Br, I, $C_1$-$C_4$ alkyl, $C_1$-$C_4$ alkoxy, $C_1$-$C_4$ haloalkyl, $C_1$-$C_4$ haloalkoxy, and nitro; and n is 1, 2, 3, or 4;

g. creating a third mixture containing the compound of Formula E2;

a fluorinating compound or a fluorinating mixture of compounds; and a solvent;

h. heating the third mixture at a temperature from about 25° C. to about 110° C.;

i. isolating from the third mixture a compound of Formula F2

Formula F2

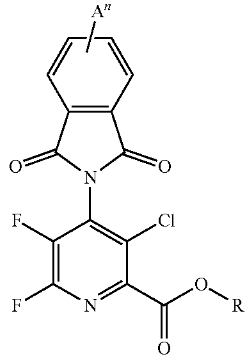

wherein

R represents H, $C_1$-$C_{12}$ alkyl, $C_3$-$C_{12}$ alkynyl, $C_1$-$C_3$ alkyl substituted with CN, or $C_6$-$C_{12}$ arylalkyl;

A is independently selected from H, F, Cl, Br, I, $C_1$-$C_4$ alkyl, $C_1$-$C_4$ alkoxy, $C_1$-$C_4$ haloalkyl, $C_1$-$C_4$ haloalkoxy, and nitro; and n is 1, 2, 3, or 4;

j. creating a fourth mixture containing the compound of Formula F2;

hydrobromic acid (HBr); acetic acid; and water;

k. heating the fourth mixture at a temperature from about 50° C. to about 110° C.;

l. Isolating from the fourth mixture the compound of Formula A or the hydrobromide (HBr) salt thereof Formula A

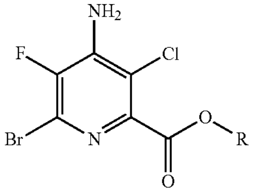

wherein

R represents H.

6. The process of claim 5, the process further comprising the steps of:

a. creating another mixture containing the compound of Formula A, wherein R represents H; and one of i. an acid, an alcohol ROH, and a solvent; or ii. an alkyl, alkynyl, or arylalkyl halide $RX^1$, a base, and a solvent wherein R represents $C_1$-$C_{12}$ alkyl, $C_3$-$C_{12}$ alkynyl, $C_1$-$C_3$ alkyl substituted with CN, or $C_6$-$C_{12}$ arylalkyl; and $X^1$ represents $C_1$, Br, or I; and b. heating the mixture at a temperature from about 25° C. to about 80° C.

7. The process of claim 6, wherein the compound of Formula A

Formula A

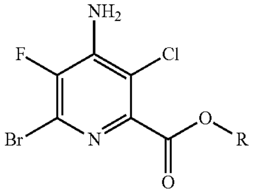

wherein

R represents $C_1$-$C_{12}$ alkyl, $C_1$-$C_3$ alkyl substituted with CN, $C_3$-$C_{12}$ alkynyl, or $C_6$-$C_{12}$ arylalkyl;

is isolated.

8. The process of claim 1, wherein the compound of Formula A is cyanomethyl 4-amino-6-bromo-3-chloro-5-fluoropicolinate.

9. The process of claim 1, wherein the compound of Formula A is 4-amino-6-bromo-3-chloro-5-fluoropicolinic acid.

10. The process of claim 1, wherein the compound of Formula B1 or Formula B2 is selected from the group consisting of (1-(tert-butyldimethylsilyl)-7-fluoro-1H-indol-6-yl) boronic acid, lithium (1-(tert-butyldimethylsilyl)-7-fluoro-1H-indol-6-yl)trimethoxyborate, lithium (1-(tert-butyldimethylsilyl)-7-fluoro-1H-indol-6-yl) triisopropoxyborate, (7-fluoro-1H-indol-6-yl) boronic acid, 7-fluoro-6-(4,4,5,5-tetramethyl-1,3,2-dioxaborolan-2-yl)-1H-indole, and mixtures thereof.

11. The process of claim 1, wherein the one or more solvents is selected from the group consisting of methyl isobutyl ketone (MIBK), dimethoxyethane (DME), acetonitrile (MeCN), tetrahydrofuran (THF), methanol (MeOH), benzyl alcohol, toluene, water, and mixtures thereof.

12. The process of claim 11, wherein the one or more solvents is acetonitrile and water.

13. The process of claim 1, wherein the first mixture is deoxygenated prior to addition of the palladium catalyst and optionally, the ligand.

14. The process of claim 1, wherein the ligand is selected from the group consisting of tri-tert-butylphosphine, tricyclohexylphosphine, di-tert-butylphenylphosphine, dicyclohexylphenylphosphine, triphenylphosphine, tri (o-tolyl) phosphine, 1,2-bis(diphenylphosphino) ethane, 1,3-bis (diphenylphosphaneyl) propane, 1,4-bis (diphenylphosphino) butane, 1,1'-ferrocenediyl-bis (diphenylphosphine) (dppf), 4-diphenylphosphinomethyl polystyrene resin crosslinked, sodium diphenylphosphinobenzene-3-sulfonate with 2% DVB, tri (p-tolyl)phosphine, and (+)-2,2'-bis(diphenylphosphino)-1,1'-binaphthyl.

15. The process of claim 14, wherein the ligand is triphenylphosphine.

16. The process of claim 1, wherein the palladium catalyst is selected from the group consisting of palladium acetate ($Pd(OAc)_2$) and dichlorobis(triphenylphosphine) palladium (II) ($PdCl_2(PPh_3)_2$).

17. The process of claim 1, wherein the base is selected from the group consisting of potassium carbonate, potassium bicarbonate, sodium carbonate, sodium bicarbonate, potassium acetate, sodium acetate, potassium phosphate monobasic, potassium phosphate dibasic, potassium phosphate tribasic, sodium tetraborate, potassium hydroxide, sodium hydroxide, cesium fluoride, potassium fluoride, triethylamine, triisopropylamine, diisopropylamine, diethylamine, and diisopropylethylamine.

18. The process of claim 17, wherein the base is sodium hydroxide.

* * * * *